United States Patent [19]

Fogarty et al.

[11] Patent Number: 5,584,842
[45] Date of Patent: *Dec. 17, 1996

[54] VALVULOTOME AND METHOD OF USING

[75] Inventors: Thomas J. Fogarty, Portola Valley; Thomas A. Howell, Palo Alto; Jan R. Wicherski, Palm Springs; Stephen A. Sosnowski, Oceanside, all of Calif.

[73] Assignee: Intramed Laboratories, Inc., San Diego, Calif.

[ * ] Notice: The term of this patent shall not extend beyond the expiration date of Pat. No. 5,514,151.

[21] Appl. No.: 253,929

[22] Filed: Jun. 30, 1994

Related U.S. Application Data

[63] Continuation-in-part of Ser. No. 985,131, Dec. 2, 1992, abandoned.

[51] Int. Cl.[6] .......................... A61B 17/22; A61B 17/32; A61B 17/34; A61D 1/02
[52] U.S. Cl. .......................... 606/159; 606/167; 606/185
[58] Field of Search .............................. 606/1, 106, 110, 606/113, 127, 159, 167, 170, 171, 174, 181, 183, 185, 205–207; 30/151, 162, 339; 128/898

[56] References Cited

U.S. PATENT DOCUMENTS

| 5,069,679 | 12/1991 | Taheri | 606/159 |
| 5,133,725 | 7/1992 | Quadri | 606/159 |
| 5,152,771 | 10/1992 | Sabbaghian et al. | 606/159 |
| 5,318,582 | 6/1994 | Chow | 606/170 |

Primary Examiner—Glenn Dawson
Attorney, Agent, or Firm—Limbach & Limbach; Raymond Sun

[57] ABSTRACT

A valvulotome for disrupting vein valves in in-situ procedures, and for distrupting the vein valves in vein segments to be used in CABG procedures. The valvulotome includes an elongate blade mounting member and a thin, scythe-shaped cutting blade. The cutting blade is mounted relative to the blade mounting member such that the plane defined by the blade lies on the axis defined by the blade mounting member. The cutting blade has a fixed end, a free end, a cutting edge and a blunt back edge. The fixed end is fixedly attached to a distal portion of the blade mounting member. The sharpened edge faces towards the blade mounting member, which protects the vein from the sharpened edge. The sharpened edge arcs outwards and proximally from the distal portion of the blade mounting member, and terminates in a proximal portion, spaced from the blade mounting member. The blunt back edge is opposite the sharpened edge, facing the vein. The free end is opposite the fixed end and connects the blunt back edge to the proximal portion of the sharpened edge. The free end including a blunt proximal-facing portion that forms a continuation of the blunt back edge.

31 Claims, 14 Drawing Sheets

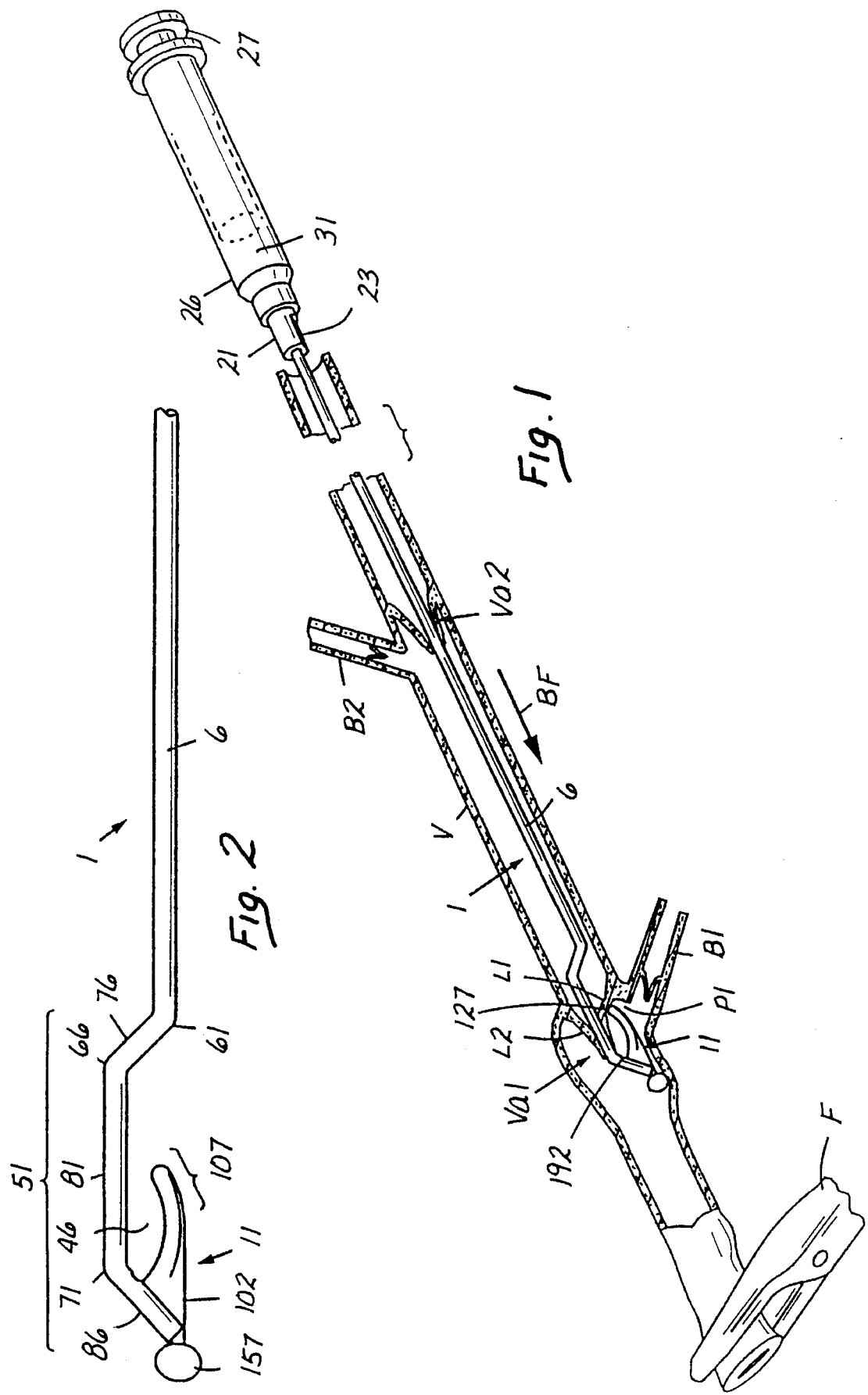

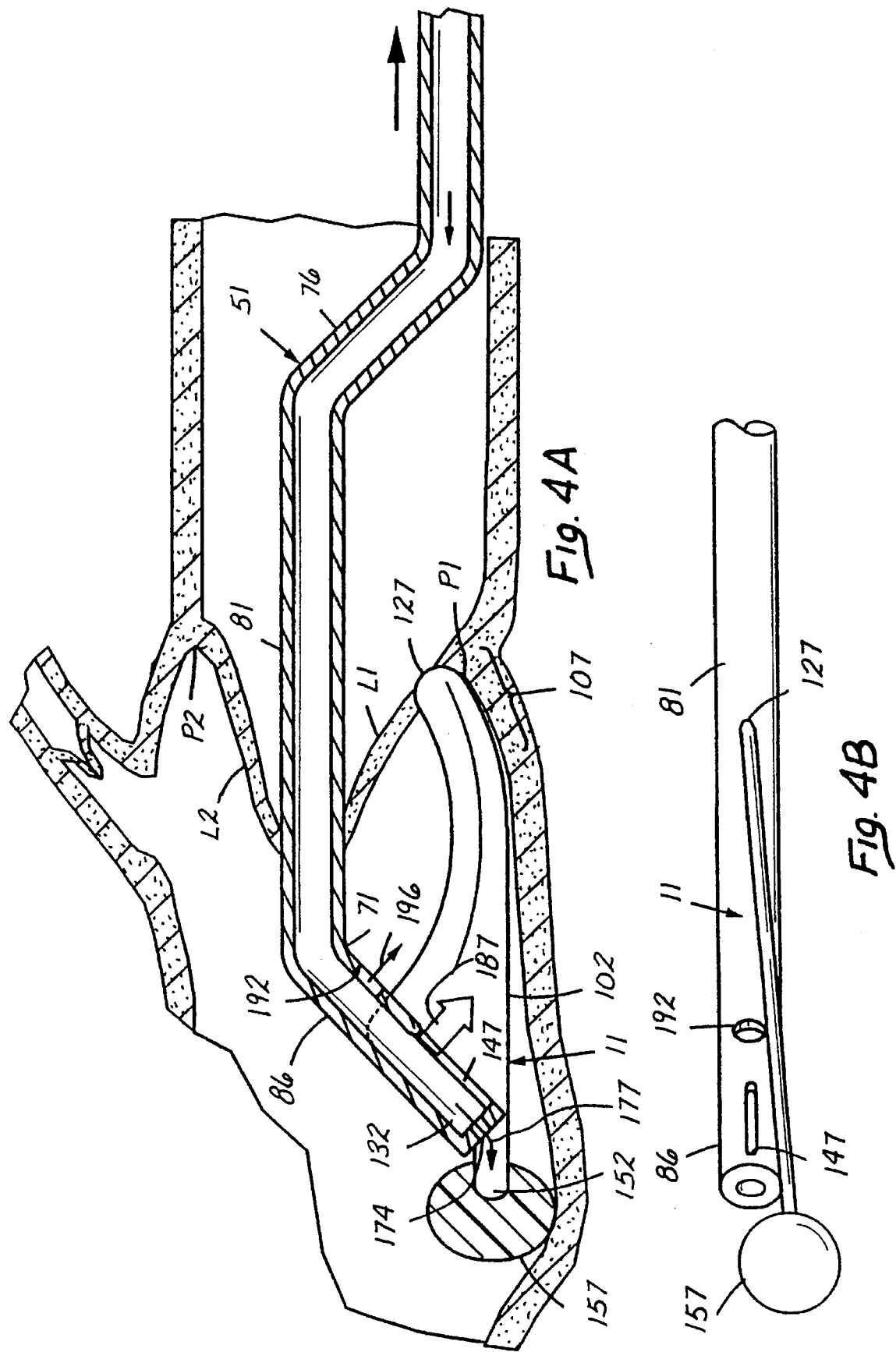

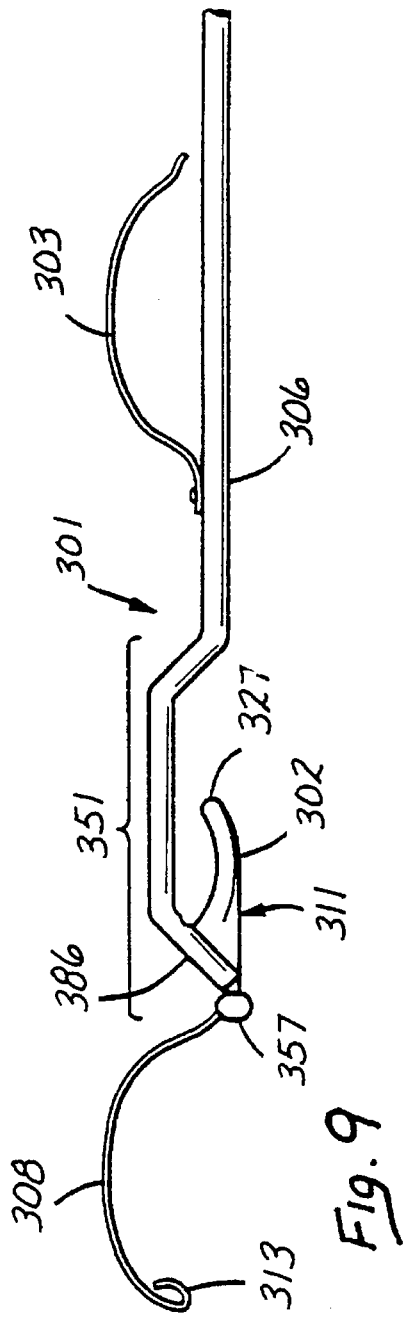
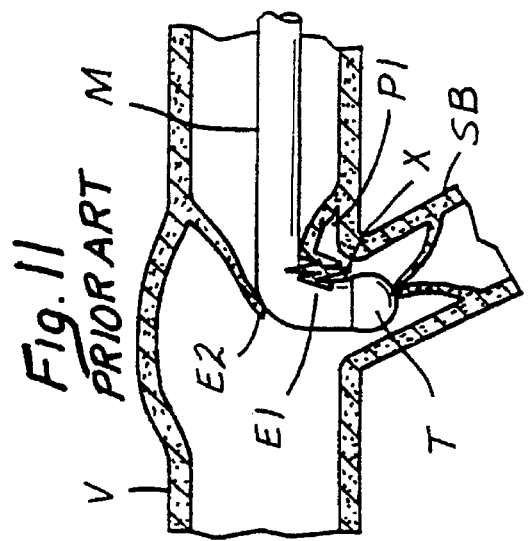
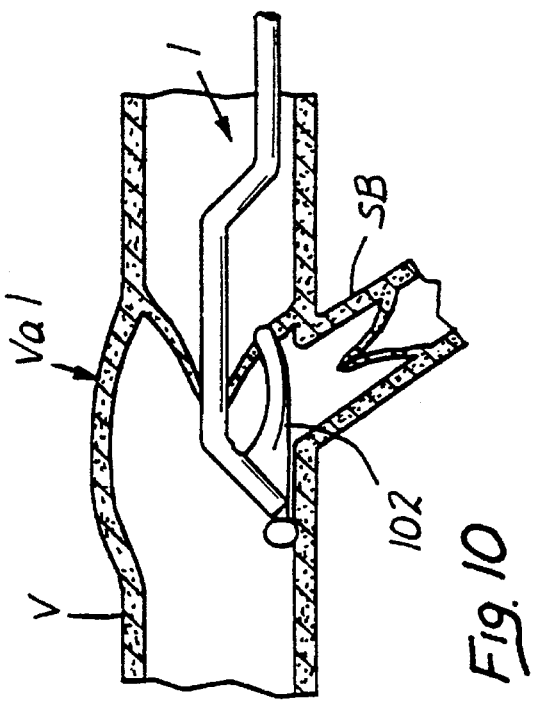

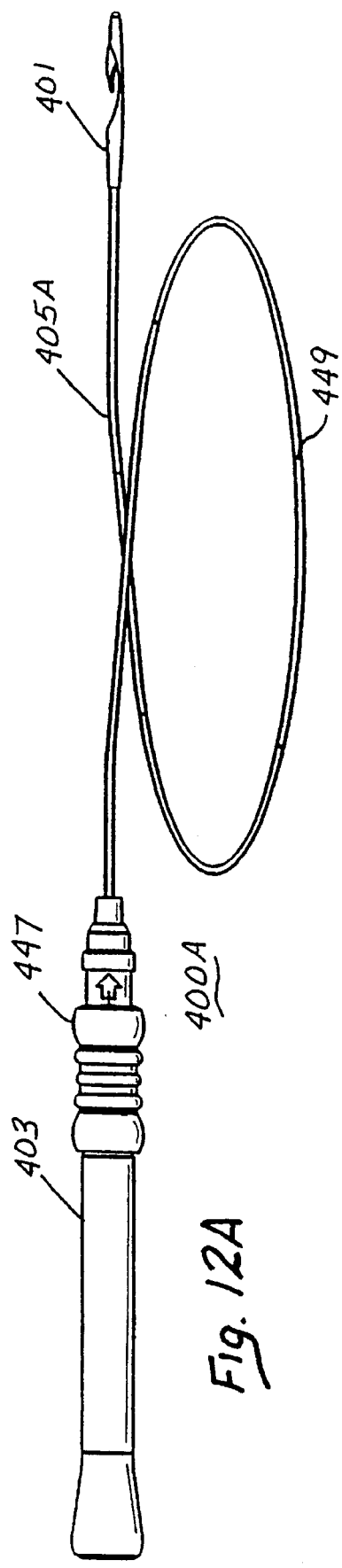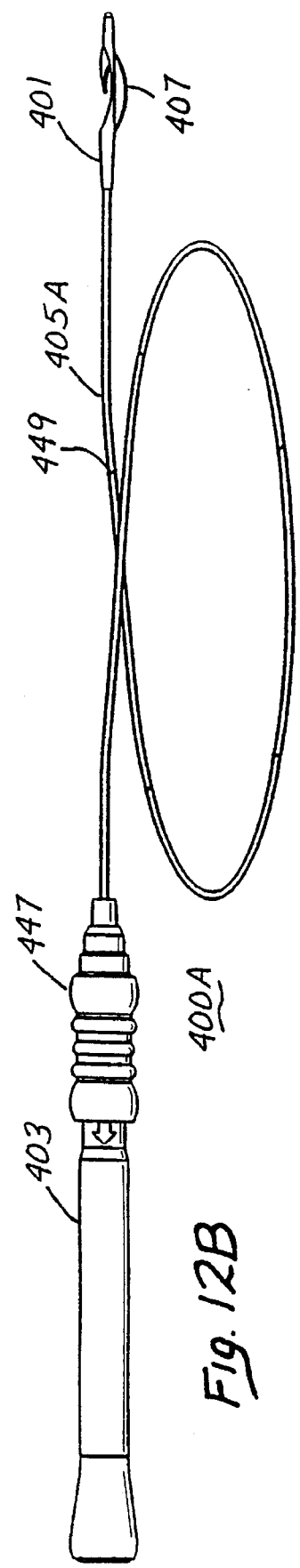

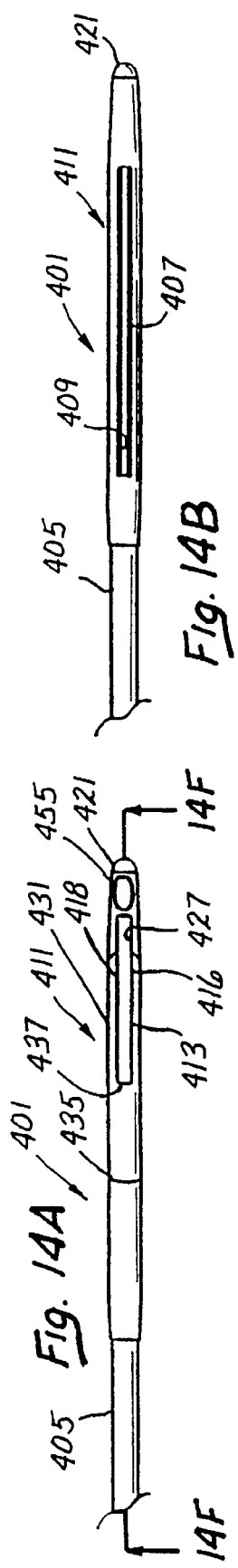
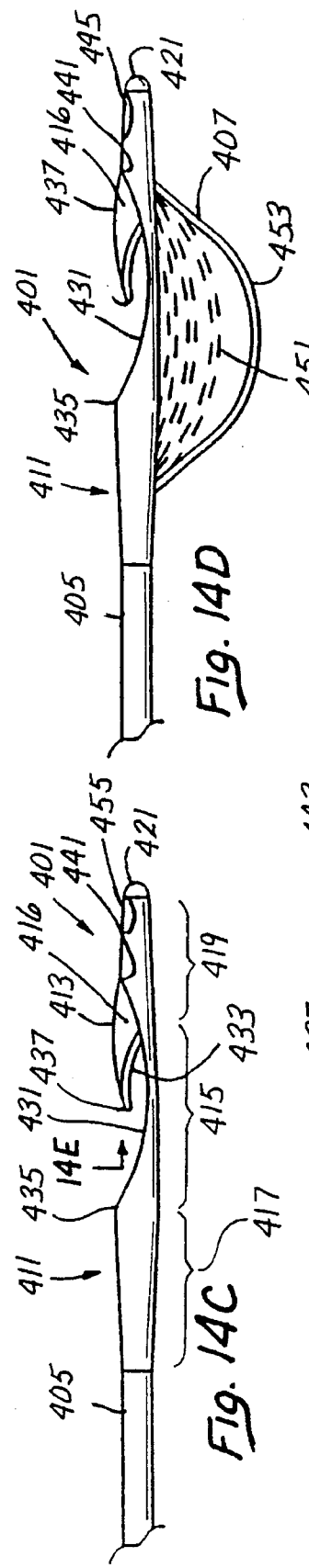
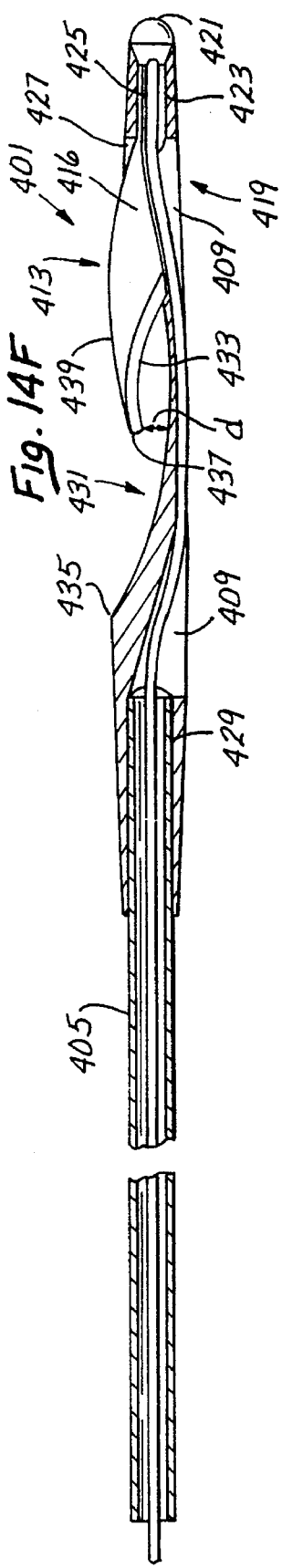

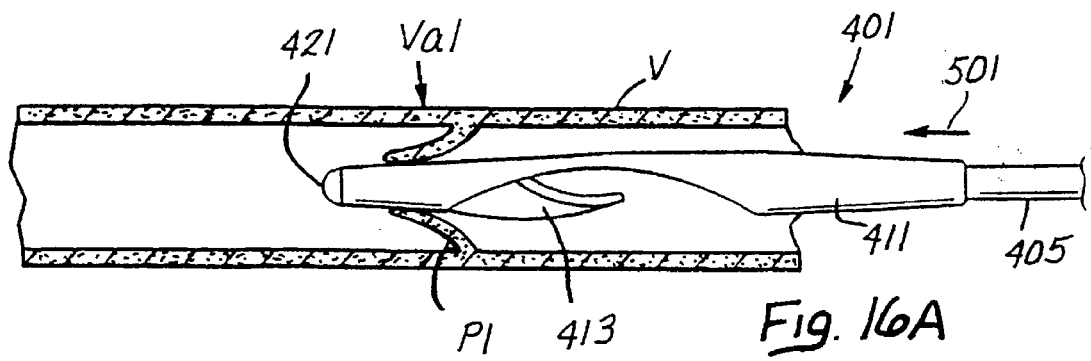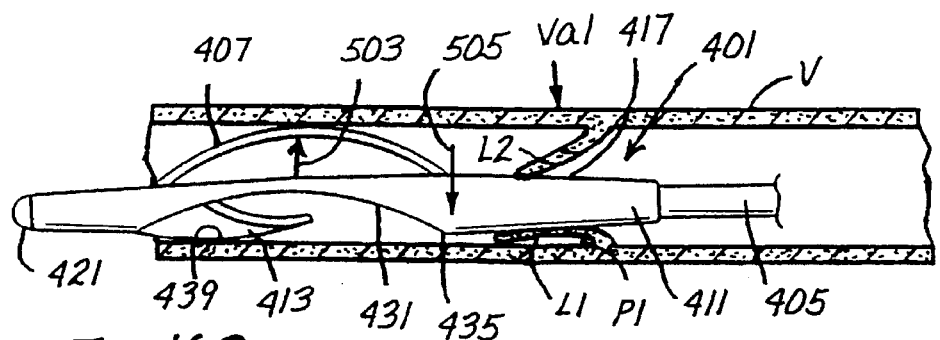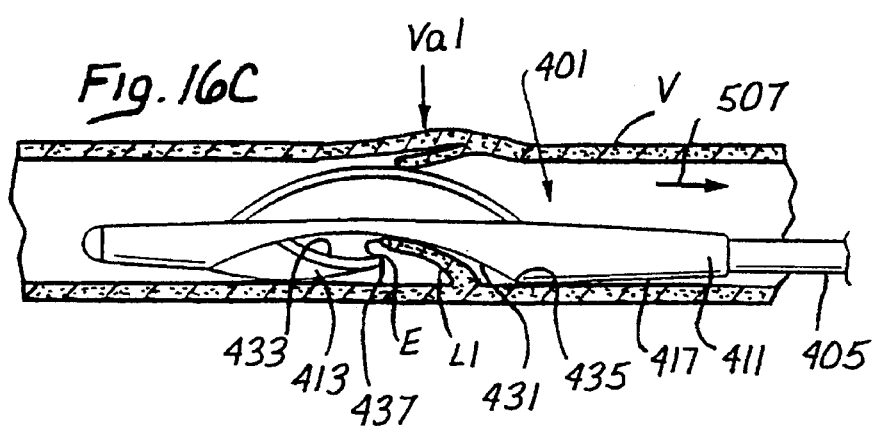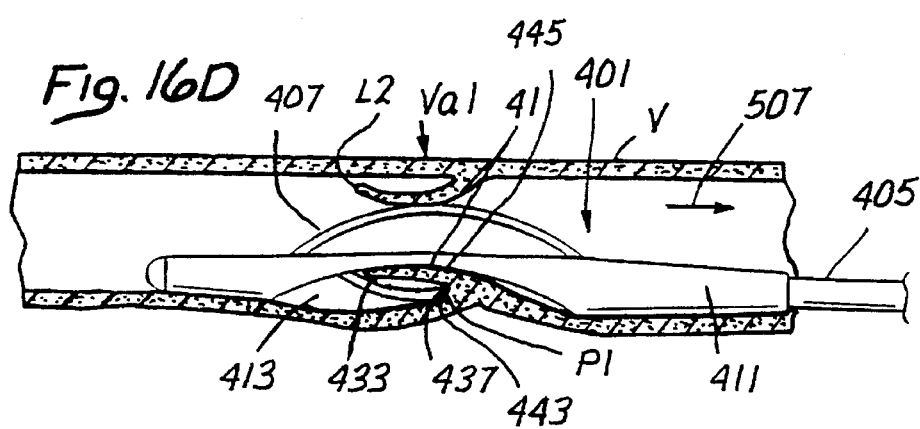

VALVULOTOME AND METHOD OF USING

PRIOR APPLICATIONS

This application is a continuation-in-part of prior application Ser. No. 07/985,131, filed 2 Dec. 1992, of Thomas J. Fogarty and Thomas A. Howell, now abandoned.

FIELD OF THE INVENTION

The present invention relates to a vein valve cutter (also called a valvulotome) for use in disrupting venous valves during vascular reconstructive surgery. In particular, the invention relates to apparatus for disrupting venous valves in vein segments for use in coronary artery bypass graft (CABG) procedures, and also for use in in situ bypass procedures, and to methods of using the apparatus to disrupt vein valves in such procedures.

BACKGROUND OF THE INVENTION

In CABG procedures, occlusive disease in the coronary arteries is routinely bypassed with segments of saphenous vein removed from the leg. It is advantageous to place the saphenous vein used as the bypass conduit in the non-reversed orientation. For the saphenous vein to be used in the nonreversed orientation, the valves of the vein must be rendered incompetent. Even if the saphenous vein is used in the reversed orientation, the valves of the vein must be rendered incompetent, since competent valve leaflets can be a site for future clot formation behind the leaflet, which can compromise the viability of the graft.

In in situ bypass procedures, occlusive disease in the arterial system of the leg is bypassed with a segment of adjacent saphenous vein left undissected from the surrounding tissue. For blood to flow in its new direction, the valves in the saphenous vein segment must be obliterated. In this procedure, it is often desirable to view the valve-cutting process directly using a fiber optic scope inserted into the vein.

In both the CABG and the in situ procedures, an infusion of physiologic solution into the vein is useful to identify the valve by clearing the field of view and temporarily closing the valves.

Previous efforts to disrupt the valves within a vein have led to a number of devices and techniques.

One form of valvulotome, called a Mills valvulotome, consists of a long, thin shaft with a short, narrow blade at its distal end. The blade is approximately perpendicular to the longitudinal axis of the shaft. The end of the blade remote from the shaft has a small spherical tip. The blade has a cutting edge along substantially all of its proximal edge, while the distal edge is dull.

A significant shortcoming of the L-shaped design of the Mills valvulotome is the propensity for the blade to snag on side branches of the saphenous vein. This tendency is both cumbersome for the surgeon and also can compromise the integrity of the vein graft. The blade of the Mills valvulotome is small enough to enter side branches easily and, once engaged within the branch, can cut the wall of the vein.

Another type of valvulotome design consists of a wire with a large bullet-shaped tip and round guide pulled by a catheter. The cutting element is located at the proximal end of the bullet tip. Valvulotomes of this design include the LeMaitre, Leather, Hall and Insitucat styles. This design is less prone to catching in side branches but has the disadvantages of being bulky, incompatible with angioscopy for visualization of the cutting-process, and is effective only over a narrow range of vein diameters. Also, the Leather, Hall and Insitucat designs require proper rotational orientation to align properly with the valve cusps, a requirement that is difficult to achieve, given their incompatibility with fiber optic viewing. Moreover, devices of this design tend to tear the valve instead of cut it because the cutting force is simultaneously applied to a relatively large area of the valve.

In another valvulotome design, the valve is cut by a plurality of blunt fingers extending from the end of a catheter. The cutter fingers are shielded except when exposed by the user to engage the valve. A fiber optic viewer extends up the center bore of the catheter to directly observe the cutting process. In this design, the fiber optics are an integral pan of the valvulotome. This design, with its many moving parts, has the disadvantage of being difficult to manufacture. Moreover, the fingers' bluntness, as well as their plurality, tend to rip the valve in a random manner, leaving the vein wall in an unpredictable condition.

OBJECTS AND SUMMARY OF THE INVENTION

Therefore, it is an object of the present invention to produce a valvulotome that simplifies the operation of disrupting the valves in a vein; reduces the tendency to snag side branches, yet easily engages and aligns with the valves to be cut; and truly cuts the valve neatly.

It is also an object of the present invention to provide a version of the valvulotome that is capable of providing fluid irrigation.

It is a further object of the invention to provide a valvulotome that can be used either with, or without direct visualization, and that is inherently simple to manufacture.

Accordingly, the invention provides a valvulotome that comprises an elongate blade mounting member and a thin, scythe-shaped cutting blade. The cutting blade is mounted relative to the blade mounting member such that the plane defined by the blade lies on the axis defined by the blade mounting member. The cutting blade has a fixed end, a free end, a cutting edge and a blunt back edge. The fixed end is fixedly attached to a distal portion of the blade mounting member. The sharpened edge faces towards the blade mounting member, which protects the vein from the sharpened edge. The sharpened edge arcs outwards and proximally from the distal portion of the blade mounting member, and terminates in a proximal portion, spaced from the blade mounting member. The blunt back edge is opposite the sharpened edge, facing the vein. The free end is opposite the fixed end and connects the blunt back edge to the proximal portion of the sharpened edge. The free end including a blunt proximal-facing portion that forms a continuation of the blunt back edge.

A portion of the blade mounting member, proximal of the distal portion, may be shaped to provide a blade recess accommodating the sharpened edge and the free end of the cutting blade. The blade recess further protects the vein from the sharpened edge and the sharp part of the free end of the cutting blade.

The blade recess may include a proximal portion shaped to provide a shoulder adjacent, and spaced from, the free end of the cutting blade to provide yet further protection for the vein.

The valvulotome may also include an extendable device, such as an extendable guide wire, that selectively moves the cutting blade laterally in the vein to assist the proximal end of the cutting blade to enter the valve pocket, prior to cutting the valve. The extension of the extendable device is adjustable to enable the valvulotome to be used in veins of different diameters, or to accommodate the change in diameter that occurs along the length of a single vein.

The blade mounting member may comprise an elongate shaft and an extension extending distally from the distal portion of the shaft in a laterally offset relation to the shaft. The extension would include a distal portion to which the fixed end of the cutting blade is attached.

Alternatively, the blade mounting member may comprise an elongate shaft and a substantially cylindrical haft extending distally from the distal portion of the shaft. The haft would include a blunt nose remote from the elongate shaft, a curved surface, a blade recess formed in the curved surface, and a distal portion to which the fixed end of the cutting blade is attached with the cutting edge and the free end in the blade recess.

The invention also provides a valvulotome comprising an elongate shaft, a substantially cylindrical, blunt-nosed haft, a thin, scythe-shaped cutting blade, a guide wire, and a device for selectively extending an extending portion of the guide wire. The haft includes a distal portion, a curved surface, a blade recess formed in the curved surface, and a bore communicating with a slot formed in a portion of the curved surface opposite the blade recess. The cutting blade is mounted relative to the haft such that the plane defined by the cutting blade is on the axis defined by the shaft.

The cutting blade includes a fixed end, a free end, a sharpened edge and a blunt back edge. The fixed end is fixedly attached to the distal portion of the haft. The sharpened edge faces into the blade recess, arcs outwards and proximally from the distal portion of the blade mounting member, and terminates in a proximal portion spaced from the haft and accommodated by the blade recess. The blunt back edge is opposite the sharpened edge, facing the vein. The free end is opposite the fixed end, and connects the blunt back edge to the proximal portion of the sharpened edge. The free end includes a blunt proximal-facing portion forming a continuation of the blunt back edge.

The guide wire is slidably mounted in the bore, and includes an extending portion adjacent the slot. The device for selectively extending the extending portion of the guide wire selectively slides a proximal portion of the guide wire relative to the bore, which selectively extends the extending portion of the guide wire from the slot.

The valvulotome presents to the wall of the vein two relatively large, blunt surfaces: to one side, the back edge of the blade; and, to the other side, the back of the blade mounting member. The dimensions of the surfaces that the valvulotome presents to the wall of the vein are larger than the diameter of the entries of side branches of the vein, which makes the valvulotome automatically reject entry into such side branches. Moreover, the broad, blunt surfaces of the valvulotome significantly reduce the possibility of the valvulotome penetrating the wall of the vein compared with known valvulotomes. Finally, the cutting edge of the blade of the valvulotome is shielded by the blade mounting member. Therefore, the valvulotome may be allowed to make contact with the walls of the vein since there is minimal risk of the valvulotome damaging the vein. This allows the valvulotome to be self guiding as it is advanced up the vein, and enables the surgeon to use the valvulotome without internal observation.

Finally, the invention provides a method of performing a valvotomy. A valvulotome is provided that includes an elongate blade mounting member and a thin, scythe-shaped cutting blade. The cutting blade is mounted relative to the blade mounting member such that the plane defined by the blade lies on the axis defined by the blade mounting member. The cutting blade has a fixed end, a free end, a cutting edge and a blunt back edge. The fixed end is fixedly attached to a distal portion of the blade mounting member. The sharpened edge faces towards the blade mounting member, which protects the vein from the sharpened edge. The sharpened edge arcs outwards and proximally from the distal portion of the blade mounting member, and terminates in a proximal portion, spaced from the blade mounting member. The blunt back edge is opposite the sharpened edge, facing the vein. The free end is opposite the fixed end and connects the blunt back edge to the proximal portion of the sharpened edge. The free end including a blunt proximal-facing portion that forms a continuation of the blunt back edge.

The cutting blade is moved towards the valve to automatically locate the free end of the cutting blade at the apex. The leaflet is pierced at the apex using the free end of the cutting blade. Finally, a tensile force is applied between the cutting blade and the leaflet to cut the leaflet from the apex to the edge.

The valvulotome may additionally include an extendable guide wire mounted on a side of the blade mounting member remote from the cutting blade. The extendable guide wire is in a retracted state. Then, the step of moving the cutting blade towards the valve to automatically locate the proximal end of the cutting blade at the apex would include the step of selectively extending the extendable guide wire to an extended state to move the cutting blade laterally in the vein. This enables the free end of the cutting blade to enter the valve pocket easily.

When the cutting blade is moved towards the valve, the blade mounting member is moved until the free end of the cutting blade contacts the leaflet, and advances along the leaflet to the apex. When the leaflet is pierced, the blade mounting member is further moved until the free end pierces the leaflet at a point. Finally, when a tensile force is applied between the cutting blade and the leaflet to cut the leaflet, the blade mounting member is withdrawn yet further to pull the cutting edge of the cutting blade through the leaflet from the point where the leaflet was pierced to the edge of the leaflet.

The apex of the valve pocket corresponds to the center of the leaflet and is most proximal, and the method cuts the leaflet substantially along the center of the leaflet. When the cutting blade is moved towards the valve, the valvulotome is allowed to rotate axially to locate the free end of the cutting blade in the apex of the valve pocket.

The valvulotome may include a traction point and be advanced through the vein using a suture. When the cutting blade is moved towards the valve, a suture is provided and is advanced through the vein. The suture is attached to the traction point, and the suture is drawn on to pull the valvulotome through the vein until the cutting blade has passed through the valve. Finally, the blade mounting member is withdrawn to move the cutting blade towards the valve.

When the cutting blade is moved towards the valve, the vein may be gripped adjacent its distal end to seal the vein. The valvulotome is then advanced through the vein to a point adjacent the distal end and a fluid is emitted from the valvulotome to inflate the part of the vein between the distal end and the valve. The position of the valve in the vein is then determined by observing the inflated part of the vein.

The method may additionally comprise the step of emitting fluid from the valvulotome to impinge on the leaflet adjacent to the cutting blade to displace the leaflet away from the vein, prior to moving the cutting blade towards the valve.

The method may be performed by a surgeon without assistance. Prior to moving the cutting blade towards the valve, the surgeon holds the proximal end of the vein in his/her first hand and holds the blade mounting member in his/her second hand. The surgeon inserts the cutting blade into the proximal end of the vein, and advances the cutting blade through the valve. The surgeon then moves his/her first hand to grip and seal the distal end of the vein. Then, with his/her second hand, the surgeon causes the valvulotome to emit fluid which inflates the vein. When the cutting blade is moved towards the valve, surgeon withdraws the blade mounting member using his/her the second hand.

BRIEF DESCRIPTION OF THE DRAWINGS

FIG. 1 shows a perspective view of a valvulotome according to the invention attached to a syringe, inserted in a vein, and in position to cut a first leaflet.

FIG. 2 shows an elevational view of a valvulotome according to the invention.

FIG. 4A shows a cross sectional view of part of a valvulotome according to the invention after it has pierced the apex of one leaflet and shows the flow of physiologic solution.

FIG. 4B is an edge view of the head of a valvulotome according to the invention showing the tip, the dull edge of the blade, and the jet hole.

FIG. 9 is a side view of a valvulotome equipped with convex spring parts according to the invention.

FIG. 10 is a side view of a valvulotome according to the invention in a vein showing how the shape of the valvulotome prevents it from entering a side branch of the vein.

FIG. 11 is a side view of a prior art Mills valvulotome in a vein showing the tendency of such a valvulotome to enter a side branch of the vein when the prior art valvulotome is correctly oriented to cut a valve leaflet. The figure also shows how the Mills valvulotome places the leaflet in compression while cutting the leaflet.

FIG. 12A is a view of a version of the preferred embodiment of the valvulotome according to the invention for use in in-situ procedures.

FIG. 12B is a view of the preferred embodiment of the valvulotome shown in FIG. 12A with its guide wire extended.

FIG. 14A is a top view of valve cutter of the embodiments of the valvulotome shown in FIGS. 12A and 13A.

FIG. 14B is a bottom view of valve cutter of the embodiments of the valvulotome shown in FIGS. 12A and 13A.

FIG. 14C is a side view of valve cutter of the embodiments of the valvulotome shown in FIGS. 12A and 13A.

FIG. 14D is a side view of valve cutter of the embodiments of the valvulotome shown in FIGS. 12A and 13A showing extension of the guide wire.

FIG. 14E is an end view of the cutting blade in the embodiments of the valvulotome shown in FIGS. 12A and 13A.

FIG. 14F is a cross sectional view of the valve cutter in the embodiments shown in FIGS. 12A and 13A.

FIG. 16A shows part of the preferred embodiment of the valvulotome according to the invention in a vein being advanced in the blood-flow direction through the vein.

FIG. 16B shows part of the preferred embodiment of the valvulotome according to the invention in the vein being advanced through a valve in the vein.

FIG. 16C shows part of the preferred embodiment of the valvulotome according to the invention in the vein being withdrawn through the valve with the edge of the leaflet in the blade recess.

FIG. 16D shows part of the preferred embodiment of the valvulotome according to the invention in the vein being withdrawn through the valve with the free end of the cutting blade engaged in the valve pocket.

DETAILED DESCRIPTION OF THE INVENTION

Figure 3A:
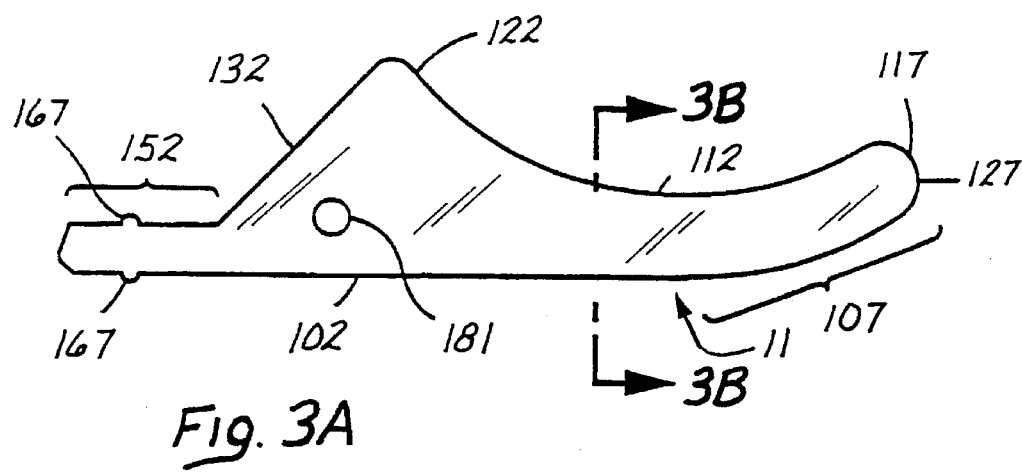
FIG. 3A shows a plan view of the blade of a valvulotome according to the invention.

FIG. 1 shows a first embodiment of the valvulotome 1 according to the invention in position in a vein V. The valvulotome 1 is shown with its blade 11 in position in the valve pocket P1, about to pierce the apex of the leaflet L1. The vein V, normally a saphenous vein, but the valvulotome can be used in other veins, includes a valve Va1 comprising two leaflets, a first leaflet L1 and a second leaflet L2. On the distal side of the valve Va1, i.e., on the side closer to the heart, is a side branch B1. More proximal on the vein is a second valve Va2 with a second side branch B2 on its distal side. When the vein is in the leg, blood flows in the vein in the direction indicated by the arrow BF. This will be called the "normal direction".

The valvulotome 1 is shown in detail in FIG. 2. The shaft 6 is preferably made from a piece of no. 19 stainless steel tubing with an outside diameter of about 0.042" (1.1 mm), an internal diameter of 0.027"(0.7 mm), and a length of about 10.5" (265 mm). Making the shaft from stainless steel tubing provides a rigid valvulotome preferable for use in CABG procedures. The shaft 6 may also be made flexible so that the valvulotome can be used in in-situ bypass procedures. In this case, the preferred material for the shaft is ABS tubing (a terpolymer of acrylonitrile, butadiene and styrene) with the same internal diameter as no. 19 stainless steel tubing, and a somewhat larger outside diameter.

A plastic female luer hub 21 is attached with glue to the proximal end of the shaft 6. The extension 51 is laterally displaced from the shaft 6 to provide a blade recess 46 in which the blade 11 fits such that the blunt back side 102 of the blade is substantially coaxial with the shaft 6. With this arrangement, the shoulder between the shaft 6 and the extension 51 protects the vein wall from the proximal end 117 of the blade, which is sharpened over part of its circumference.

The extension 51 is preferably formed from the same piece of no. 19 stainless steel tubing as is used for the shaft 6. If an ABS shaft used, a separate stainless steel extension is formed which is then attached to the shaft. Preferably, the extension 51 is formed by making three approximately 45° degree bends 61, 66, and 71 in the stainless steel tubing. Between the bends are three substantially straight sections. Between the bends 61 and 66 is a first, short, section 76. Between the bends 66 and 71 is a second, longer, section 81 that is substantially parallel to the shaft 6. Between the bend 71 and the distal end of the extension 51 is a third, short section 86 that is substantially perpendicular to the first section 76. Bends 61 and 66 may merge into one another and, as a result, the first section 76 may lack any discernable straight part. The third bend 71 is made such that the distal end of the section 86 is substantially in line with the longitudinal axis of the shaft 6. Preferably, the extension 51 is about 0.7" (18 mm) long and 0.15"(3.8 mm) offset.

The extension 51 may be formed differently from the way just described: for example, it can have a continuous curve instead of three discrete bends. Alternatively, the third bend 71 and third section 86 can be dispensed with, and the blade 11 can be attached to the distal end of the second section 81. In this alternative, the shape of the blade 11 is changed to enable it to be attached to the second section 81 instead of the third section 86, but the distal end of the blade 11 provides substantially the same profile for the distal end of the valvulotome 1 as that shown in FIG. 2.

Figure 3B:
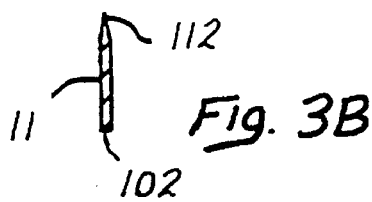
FIG. 3B shows a cross section of the blade of a valvulotome according to the invention on the line indicated in FIG. 3A.

Details of the blade 11 are shown in FIG. 3A. The blade 11 is preferably made from stainless steel about 0.008" (0.2 mm) thick, and is preferably photo etched to the profile shown in FIG. 3A. The back 102 of the blade is substantially straight over most of its length. The proximal part of the back of the blade indicated by the numeral 107 is curved into the blade recess 46. The curved part 107 of the back of the blade is also curved into the blade recess 46 so that the shoulder between the shaft 6 and the extension 51 can reduce the possibility of the proximal end 127 of the blade from snagging the wall of the vein or entering a side branch when the valvulotome is withdrawn. The curved part 107 of the back of the blade is also curved to enable the proximal end 127 of the blade to seat more deeply in the valve pocket when the walls of the vein near the valve am inflated by fluid pressure. The similarity between the curvature of the curved part 107 of the blade and the curvature of the inflated wall of the vein can be seen in FIG. 4A. The back 102 of the blade is radiused and deburred, and hence is blunt, as shown in FIG. 3B, to minimize the possibility of it damaging the vein wall.

Figure 3C:
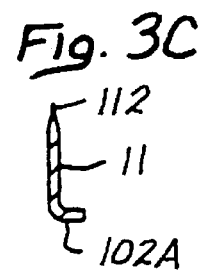
FIG. 3C shows a cross section of an alternative embodiment of the blade of a valvulotome according to the invention on the line indicated in FIG. 3A. This embodiment has a widened back.

Alternatively, the blade could be provided with a back 102A that is substantially thicker (about 0.065"–1.65 mm) than the rest of the blade, as shown in FIG. 3C. This will further reduce the possibility of damaging the vein wall. Additionally, the thicker back 102A is easier to see through the vein wall. The blade could be provided with the thicker back 102A by rolling or bending the back portion of the blade relative to the rest of the blade. Alternatively, the thicker back could be provided by injection molding as part of the bead 157.

The cutting edge 112 of the blade is opposite the back 102 of the blade, is preferably curved as shown in FIG. 3A, and is ground to give it a sharp edge between the extremities indicated by the numerals 117 and 122. The curved shape of the cutting edge 112 enables the cutting edge to cut the valve leaflet effectively while minimizing the possibility of the cutting edge accidentally damaging the vein. The curvature of the cutting edge 112 substantially matches the curvature of the curved part 107 of the back of the blade. This enables the proximal end 127 of the blade to have a relatively large radius instead of a point that would be more likely to damage the vein accidentally. The blade 11 broadens towards its distal end, which enables the cutting edge 112 to cut the leaflet all the way to the edge of the leaflet while maintaining the back 102 of the blade in contact with the wall of the vein.

As already mentioned, the proximal end 127 of the blade 11 is relatively broad and is radiused across its width. Like the back 102 of the blade, the proximal end 127 is deburred and radiused across its thickness and is therefore blunt to minimize the possibility of it accidentally damaging the vein when the valvulotome 1 is withdrawn. The proximal end 127 of the blade pierces the pocket of the valve during the cutting process, but is only able to pierce when working against the relatively high resistance provided by the leaflet (e.g., L1, L2) close to its apex (e.g., P1, P2).

Other parts of the blade 11 are concerned with mounting the blade in the extension 51. The distal end 132 of the blade is cut at about 45 degrees relative to the back 102 of the blade. The angle of the distal end 132 of the blade relative to the back 102 must match the angle between the third section 86 of the extension 51 (FIG. 2) and the shaft 6. This ensures that the back 102 of the blade is substantially parallel to the longitudinal axis of the shaft 6.

The blade 11 is preferably spot welded to one side of the third section 86 of the extension 51 such that the second section 81 of the extension 51 shields the cutting edge 112 of the blade, as shown in FIGS. 4A and 4B. The blade 11 is angled relative to the axis of the shaft 6 so that the proximal end of the blade 127 is in line with the axis of the shaft, as shown in FIG. 4B.

Alternatively, a slot 147 can be formed in the center of the inner face of the distal part of the third section 86, and the distal end of the blade 11 can be spot welded in the slot. This way, the blade is parallel to the axis of the shaft.

The blade 11 is attached to the third section 86 of the extension 51 such that the distal end of the back 102 of the blade is flush with the distal end of the third section 86. The blade 11 is also attached such that the gap between the inner part of the proximal end 127 of the blade and the second section 81 of the extension is preferably about 0.050" (1.2 mm). This distance is small enough to enable the second section 81 to effectively shield the cutting edge 112 of the blade, yet is large enough to admit the thickest part of the leaflet for cutting.

Figure 6:
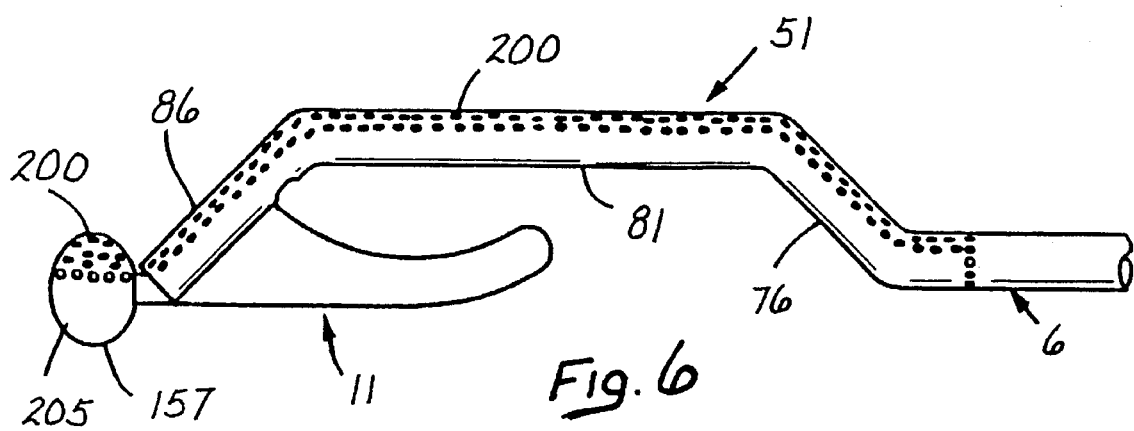
FIG. 6 is a side view of the head of a valvulotome with a spheroidal tip according to the invention. The areas of darker color are shown by shading.

The blade 11 preferably also includes the blade extension 152 on which is mounted the tip 157. The tip 157 provides the valvulotome 1 with a very dull nose. Providing the valvulotome 1 with a very dull nose ensures that the valvulotome 1 has a minimal ability to pierce as it is advanced through the vein, and thus minimizes the possibility of the valvulotome damaging the vein. FIGS. 4A, 4B, and 6 show a substantially spheroidal tip 157 of metal or plastic. The tip 157 is preferably injection molded directly around the blade extension 152. Alternatively, a molded tip 157 can be secured in place by a suitable adhesive, such as an epoxy adhesive, or the tip can be a press fit, secured by the tabs 167.

Figure 7:
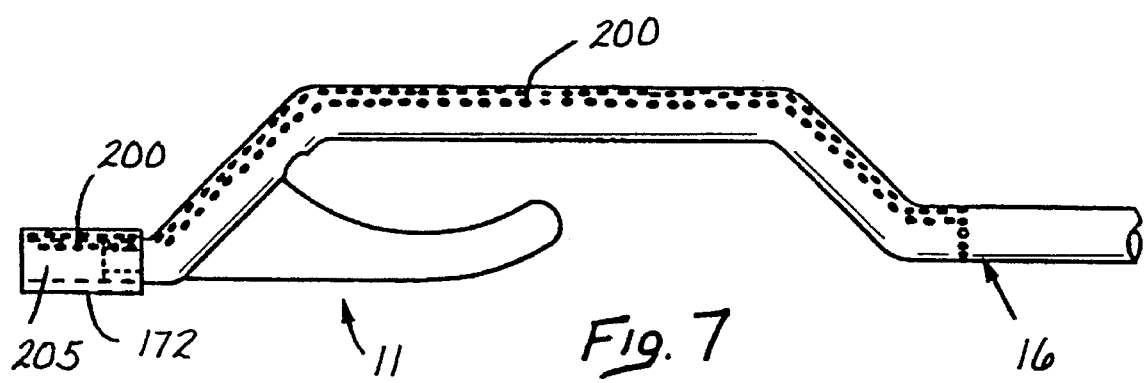
FIG. 7 is a side view of the head of a valvulotome with a flexible tip according to the invention. The areas of darker color are shown by shading.

An alternative to the spheroidal tip 157 is shown in FIG. 7 in which a flexible tip 172 is attached to the blade extension 152. The flexible tip 172 is a hollow cylindrical piece of a flexible silicone plastic and is attached to the blade extension 152 by a suitable adhesive, such as an RTV silicone adhesive, or alternatively is a push fit on the blade extension 152, secured by the tabs 167 (FIG. 3A). The flexible tip 172 is not only very dull like the spheroidal tip 157, but is also soft, which further reduces the possibility of damaging the vein when the valvulotome 1 is advanced.

The blade extension 152 may be dispensed with and a suitable tip be mounted on the end of the third section 86 (FIG. 2). Alternatively, the end of the third section 86 may be suitably flattened and shaped to provide the valvulotome 1 with a dull nose without the need for a separate component.

The blade 11 may optionally include a traction point 181 positioned about half-way across the width of the blade and positioned along the length of the blade such that it is close to the extension 51, as shown in FIG. 3A. The traction point 181 is preferably a hole about 0.03" (0.76 mm) in diameter. A suture attached to the traction point 181 enables the valvulotome 1 to be advanced through the vein by pulling on the suture. The suture applies a tensile force to the valvulotome. Pulling the valvulotome through the vein can be used as an alternative to, or in addition to, pushing the valvulotome through the vein using the column strength of the shaft 6.

The suture attached to the traction point 181 may be attached to a fiber-optic viewing scope. With this arrangement, the scope applies the tensile force to the valvulotome to advance the valvulotome up the vein. The suture maintains a fixed distance between the scope and the blade 11 of the valvulotome, which ensures that the blade remains in the field of view and in the focal plane of the scope. The suture may alternatively be attached to a catheter.

The dull nose, curved blade, and extension of the valvulotome according to the invention enable the valvulotome to be advanced and withdrawn in the vein with a minimum likelihood of causing damage. The valvulotome presents large, blunt surfaces to the walls of the valvulotome. The effective dimensions of the surfaces that the valvulotome according to the invention presents to the vein, i.e., the tip, the back of the blade, and the extension, are large compared with the diameter of side branches, enabling the valvulotome to resist entering side branches. FIG. 10 shows the valvulotome 1 being withdrawn to cut the valve Val. The length of the blade 11 is such that the blunt back 102 of the blade spans the mouth of the side branch SB. This prevents the blade from entering the side branch SB and possibly damaging the side branch SB or the vein V in the vicinity of the side branch SB.

The prior art Mills valvulotome M shown in FIG. 11 presents to the vein a surface, namely, the surface of the tip T, the effective dimensions of which are comparable with the diameter of mouth of the side branch SB. This enables the tip T accidentally to enter the mouth of the side branch SB relatively easily. The tip T entering the mouth of the side branch SB exposes the junction of the side branch SB and the vein V to the sharp cutting edge X of the Mills valvulotome. If the surgeon withdraws the valvulotome with its tip T engaged in the side branch, the valvulotome will cut down the wall of the vein V and render the vein unusable.

The arrangements for providing irrigation and inflation are shown in FIGS. 1, 4A, and 4B. The purpose of inflating the vein is to enable the location of the valves in the vein to be determined. Additionally, inflation closes the valve tightly around the shaft of the valvulotome 1, and retracts the valve away from the vein wall, improving the access of the proximal end 127 of the blade to the valve pocket P1.

In FIG. 1, the proximal end of the shaft 6 is attached to the plastic luer hub 21, onto which is screwed a standard 5 ml plastic syringe 26. The syringe 26 holds a supply of physiologic solution 31, or some other suitable fluid, and provides a means for pumping the solution 31 up to the valvulotome 1 for inflating the vein and displacing the leaflets L1 and L2. In an alternative embodiment, the length of the shaft 6 of the valvulotome is reduced to about 2.5" (65 mm), and the effective length of the valvulotome 1 is restored by attaching it to the distal end of a hollow stainless steel rod about 12" (305 mm) long. A luer hub, to which a syringe can be attached, is a push fit on the proximal end of the rod.

The valvulotome 1 can emit the physiologic solution 31 in a number of different ways. For instance, FIG. 4A shows a bore 174 in the third section 86 through which the solution is emitted in a forward direction, as indicated by the arrow 177. Alternatively, and preferably, valvulotome 1 can emit the solution 31 in a retrograde direction in a number of different ways. Emitting solution in a retrograde direction is preferable because it directs the solution towards the leaflet being cut. FIG. 4A shows a number of retrograde emission alternatives. A practical embodiment emits solution in only one or two ways. If the valvulotome 1 is not to emit solution in the forward direction, the distal end of the third section of the extension must be sealed. The tip 157 or 172 can be adapted to provide suitable sealing.

A slot 147 (FIG. 4B) can formed in the third section 86 of the extension 51, adjacent to the blade. Solution emitted from the extension 51 through the slot 147 remains in contact with the blade 11, runs down the blade in a laminar flow, as indicated by the arrow 187 (FIG. 4A), and falls off the end of the blade into the valve pocket. Alternatively or additionally, a hole 192, about 0.026" (0.66 mm) in diameter, is drilled in the wall of the third section 86 between the bend 66 and the root of the blade 11. Depending on the geometry of the hole 192, the hole 192 emits solution towards the proximal end 127 of the blade, in a jet or in a fan-shaped spray, as indicated by the arrow 196.

The direction in which the valvulotome emits solution is relatively unimportant when the solution is providing inflation prior to cutting the first leaflet L1. However, cutting the first leaflet L1 releases some pressure. The pressure may drop slowly enough for the valvulotome 1 to be advanced, rotated through 180 degrees and engaged with the second leaflet while there is still sufficient pressure to hold the leaflet L2 against the shaft of the valvulotome 1. Since the purpose of cutting the leaflet L1 is to prevent it holding pressure, sufficient pressure to hold the second leaflet L2 in place cannot be relied upon. If the pressure drops quickly, or if re-positioning the valvulotome is delayed, emitting solution towards the proximal end 127 of the blade enables the solution to impinge on the inner surface of the second leaflet L2 and to enter the valve pocket between the leaflet L2 and the vein wall. The force of the solution presses the leaflet L2 against the shaft of the valvulotome, and enables the blade to enter the valve pocket P2 to cut the second leaflet L2.

Figure 5A:
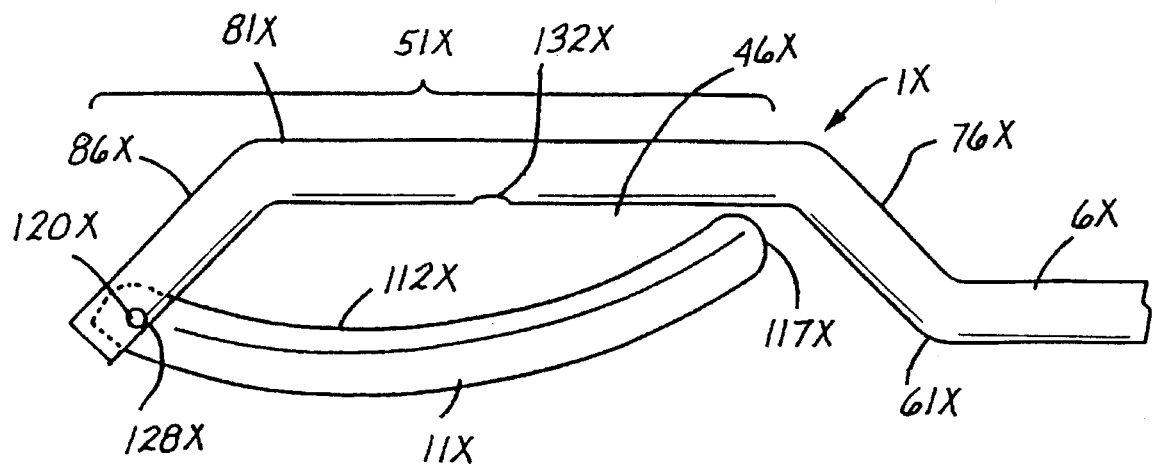
FIG. 5A is a side view of a pivoting blade valvulotome according to the invention. The blade is shown in its closed position.
Figure 5B:
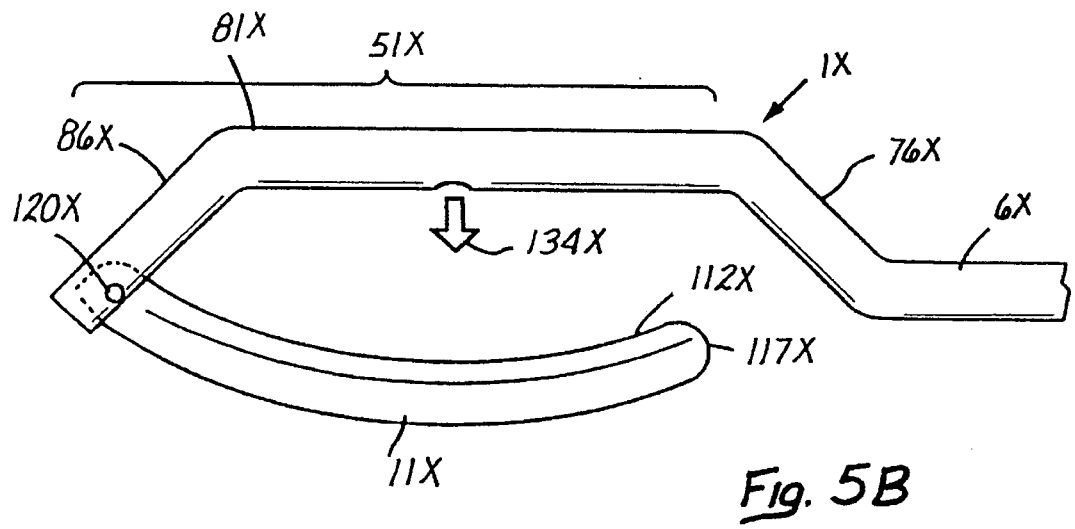
FIG. 5B is a side view of a pivoting blade valvulotome according to the invention. The blade is shown in its open position.

FIGS. 5A through 5E show several embodiments of a pivoting blade valvulotome according to the invention, in which the blade is pivotally mounted in the extension. The pivoting blade valvulotomes further reduce the risk of accidentally injuring the vein, as shown in FIGS. 5A and 5B.

FIG. 5A shows a pivoting blade valvulotome IX with its blade 11X in the closed position. In this position, the cutting edge is moved further into the blade recess 46X, closer to the extension 51X, than in the fixedblade valvulotome shown in FIG. 2. This enables the extension to provide an even greater amount of protection against the cutting edge of the blade accidentally cutting the vein. This also enables the shoulder between the shaft 6X and the extension 51X to provide an even greater amount of protection against the proximal end of the blade snagging the wall of the vein or entering a side branch. The lower profile of the pivoting blade valvulotomes allows them to be used in smaller veins.

FIG. 5A shows the proximal end 117X of the blade 11X substantially contacting the second section 81X. The degree of protection provided by the second section may be further increased by providing a slot in the second section to accommodate the blade when the blade is in the closed position.

FIG. 5B shows the pivoting blade valvulotome IX with its blade 11X swung out into the open position, just prior to cutting a leaflet. With the blade 11X in its open position, a greater clearance can be provided between the proximal end 117X of the blade and the second part 81X of the extension than in the fixed-blade valvulotome shown in FIG. 2. This makes it easier for the proximal end of the blade to enter the valve pocket.

Although the embodiments of the pivoting blade valvulotome differ in detail, they all have closed and open positions corresponding to the closed and open positions shown in FIG. 5A and 5B, respectively.

Figure 5C:
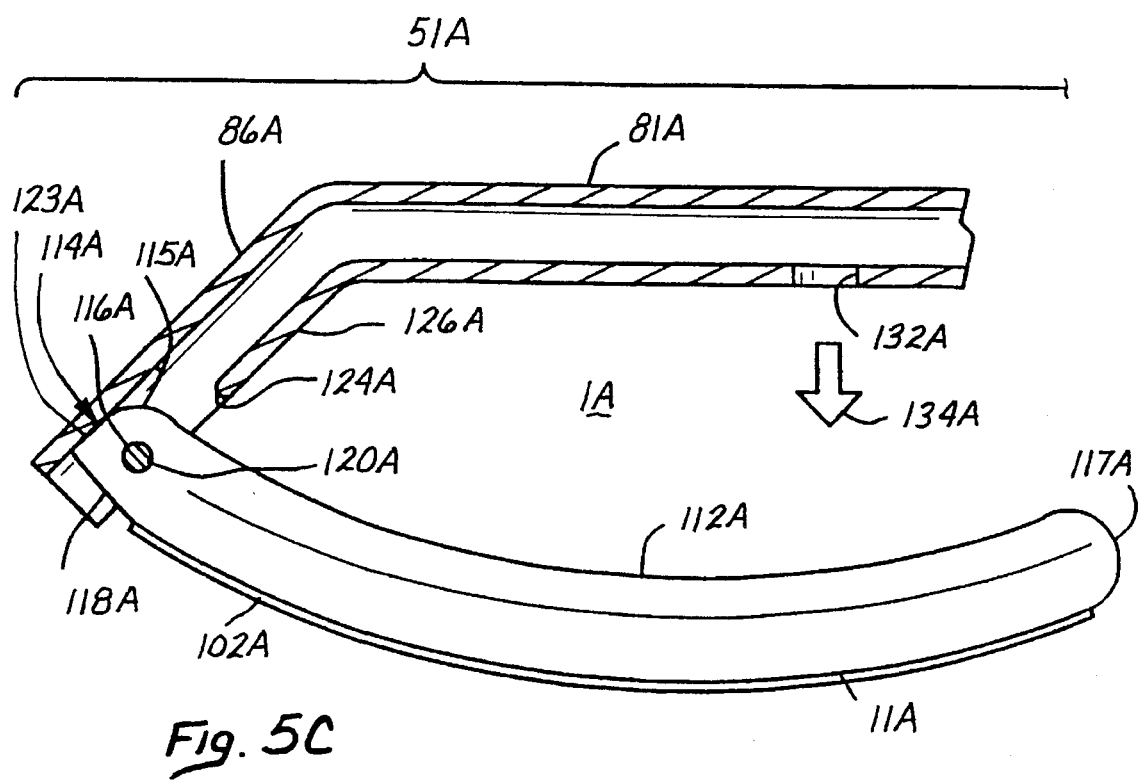
FIG. 5C is an axial cross section of a preferred embodiment of a pivoting blade valvulotome according to the invention. Details of the pivoting of the blade are shown.

A preferred embodiment of the pivoting blade valvulotome 1A according to the invention is shown in FIG. 5C. The blade 11A is similar to the blade 11 shown in FIG. 3A, except that its width is maintained substantially constant along its length, as shown in FIG. 5C. The back 102A of the blade is preferably widened, as shown in FIG. 3C.

The distal end 114A of the blade is shaped with a section 115A, which is quarter-radiused about the pivot hole 116A, and a straight section 123A. The quarter-radiused section 115A allows the blade 11A to pivot in the extension 51A until the straight section 123A juxtaposes the third section 86A. This provides a mechanical limit to the outward movement of the blade 11A in its open position.

The extension 51A is substantially similar to the extension 51 of FIG. 2, but the third section 86A is modified to accommodate the pivoting blade 11A. A slot 124A is cut in the inside face 126A of the distal-most part of the third section. The slot is wide enough to accommodate the blade 11A, and long enough to accommodate the distal portion of the blade 11A when the blade is in its closed position. The slot 124A may be extended proximally into the second section 81A of the extension 51A to accommodate all of the blade 11A, and to reduce further the risk of the cutting edge 112A of the blade 11A accidentally cutting the valve.

The pivot pin hole, similar to the pivot pin hole 128X shown in FIG. 5A, is drilled through the third section 86A, is perpendicular to the slot 124A, and accommodates the pivot pin 120A, which also passes through the pivot pin hole 116A in the blade 11A.

The valvulotome is provided with a jet hole 132A for emitting a jet of solution (indicated by the arrow 134A) towards the blade 11A. The jet of solution impinges on the blade, preferably on the widened back 102A thereof. Additional holes (not shown) may provide a flow of solution down the blade 11A.

Preferably, the blade 11A is unbiased. The blade is moved to its closed position by hand before the valvulotome is inserted into the vein. Pressure between the vein wall and the back of the blade maintains the blade in its closed position as the valvulotome is advance through the vein.

When the valvulotome is in position to cut a valve, the blade 11A is moved to its open position by a jet of solution 134A emitted by the jet hole 132A impinging on the blade, preferably on the widened back 102A thereof. Once the blade has been moved to its open position, engaging the proximal end 117A of the blade with the valve leaflet holds the blade in its open position, and the flow of solution may be discontinued if desired.

The blade may be returned to its closed position while in the vein by external pressure exerted through the vein wall by, for example, the surgeon's finger.

Figure 5D:
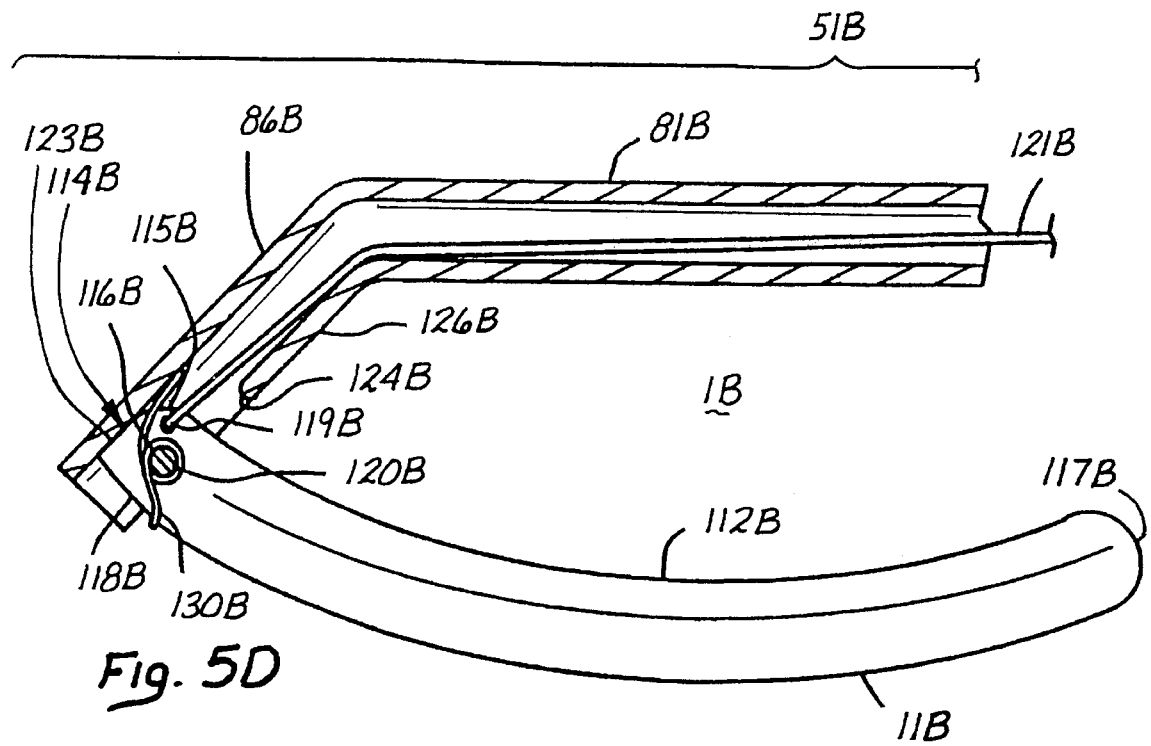
FIG. 5D is an axial cross section of a first alternative embodiment of a pivoting blade valvulotome according to the invention. Details of the pivoting of the blade and the cable operating mechanism are shown.

A first alternative embodiment of the pivoting blade valvulotome 1B is shown in FIG. 5D. In this, the blade 11B is biassed into its closed position by the hairspring 130B, and is pulled towards its open position by the operating cable 121B.

The blade 11B and its mounting in the third section 86B of the extension is substantially similar to the blade 11A and its mounting just described, and so will not be described in detail. Corresponding parts use the same reference numbers with the letter "B" instead of the letter "A".

The pivot pin 120B passes through the hairspring 130B, in addition to passing through the pivot pin hole 116B in the blade 11B, and the pivot pin hole 128B in the third section 86B. Opposite ends of the hairspring 130B contact the blade 11B and the inner wall of the third section 86B to bias the blade 11B into its closed position (FIG. 5A).

The blade 11B additionally includes the operating cable hole 119B to which the operating cable 121B is attached. The operating cable runs proximally from the blade 11B through the bore of the shaft 6B, and emerges from the shaft through a fluid-tight seal (not shown) near the proximal end of the shaft. The operating cable is preferably a stainless steel wire, about 0.008" (0.2 mm) in diameter. The operating cable may alternatively be spot welded to the blade 11B.

In use, the operating cable 121B of the alternative embodiment of the pivoting-blade valvulotome 1B is left slack while the valvulotome is advanced through the vein, as will be described in detail below. The hairspring 130B biases the blade 11B into its closed position shown in FIG. 5A. The proximity of the second section 81B to the cutting edge 112B of the blade ensures that the cutting edge of the blade will not accidentally cut the vein.

When the extension 51B of the valvulotome is positioned just beyond the valve to be cut, as will be described in detail below, the surgeon applies tension to the operating cable 121B to move the blade 11B into its operating position, spaced from the second section 81B. The operating cable is pulled until the straight section 123B of the distal end of the blade 11B abuts the third section 86B, which prevents further opening of the blade and allows the pivoted blade to exert the force necessary to cut the valve. Engaging the proximal end 117B of the blade with the valve leaflet holds the blade 11B in its open position, and tension can be removed from the operating cable 121B. This enables the blade to return automatically to its closed position after a leaflet has been cut. The blade is then re-opened using the operating cable 121B when the valvulotome is in position to cut the next leaflet.

In a variation on the pivoting blade valvulotome just described, the operating cable 121B may be dispensed with, and the blade, which would preferably have the widened back shown in FIG. 3C, may be moved into its open position by the force exerted on it by a jet of physiologic solution emerging from a jet hole in the inner face of the second section. This arrangement is similar to the arrangement in the embodiment shown in FIG. 5C, but uses a hairspring to bias the blade into its closed position. Once the blade has been moved to its open position, engaging the proximal end of the blade with the valve leaflet holds the blade in its open position, and the flow of solution may be discontinued if desired.

Figure 5E:
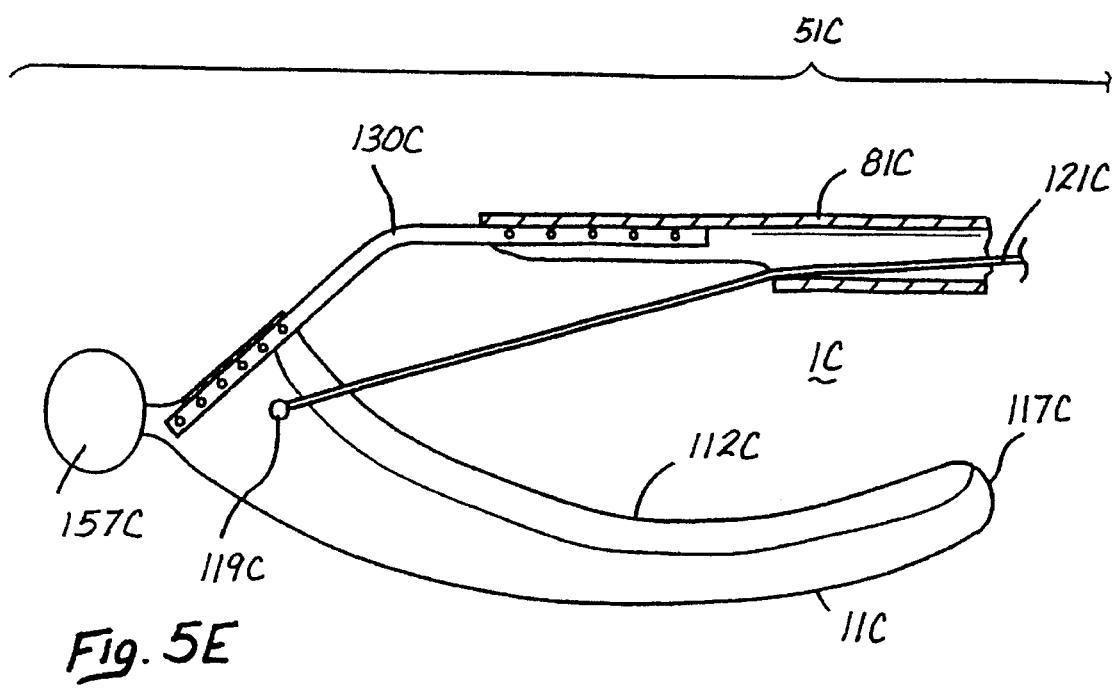
FIG. 5E is a side view of a second alternative embodiment of a pivoting blade valvulotome according to the invention.

A second alternative embodiment 1C of a pivoting blade valvulotome according to the invention is shown is FIG. 5E. In this embodiment, the blade 11C is mounted on a spring-steel blade mount that forms part of the extension. The blade mount enables the blade to move as if it were pivoted between a closed position and an open position corresponding to the closed position and the open position shown in FIGS. 5A and 5B, respectively.

Preferably, the spring-steel blade mount 130C is substituted for the third section and part of the second section 81C of the extension 51C. The second section 81C is also shaped as shown to allow the blade carrier 130C to attached to it, preferably by spot welding. The shaping of the second section 81C also provides an optimum operating angle between the operating cable 121C, which emerges from the second section, and the blade 11C.

The blade carrier is preferably a piece of spring steel wire about 0.018" (0.42 mm) in diameter, with a shape similar to that of the third section and the part of the second section of the extension that it replaces.

The blade 11C is shaped substantially the same as the blade 11 shown in FIG. 2, with the addition of the operating cable hole 119C. Alternatively, the operating cable hole can be dispensed with, and the operating cable can be attached to the blade by spot welding. The blade carries the soft tip 157C. The blade is attached to the blade carrier 130C, preferably by spot welding, such that it assumes its open position, as in FIG. 5C, when no tension is applied to the operating cable 121C.

Applying tension to the operating cable 121C causes the blade carrier 130C to flex, the blade to move to its closed position, as shown for the embodiment shown in FIG. 5A, with the proximal end 117C of the blade close to the extension 51C, and the extension 51C shielding the cutting edge 112C.

In use, tension is applied to the operating cable 121C of the movingblade valvulotome 1C to move the blade to its closed position. The valvulotome is then advanced through the vein, as will be described in detail below. The proximity of the second section 81C to the cutting edge 112C of the blade ensures that the cutting edge will not accidentally cut the vein.

When the extension 51C of the moving-blade valvulotome is positioned just beyond the valve to be cut, as will be described in detail below, the surgeon releases the operating cable 121C to move the blade 11C into its open position, spaced from the second section 81C. The valvulotome is then used normally, as will be described below, to cut the first leaflet of the valve. After the first leaflet has been cut, tension may be applied to the operating cable 121C again to return the blade to its closed position before the valvulotome is advanced up the vein to cut the second leaflet. When the valvulotome is in position to cut the second leaflet, tension is released from the operating cable to return the blade to its open position to cut the second leaflet.

Figure 8:
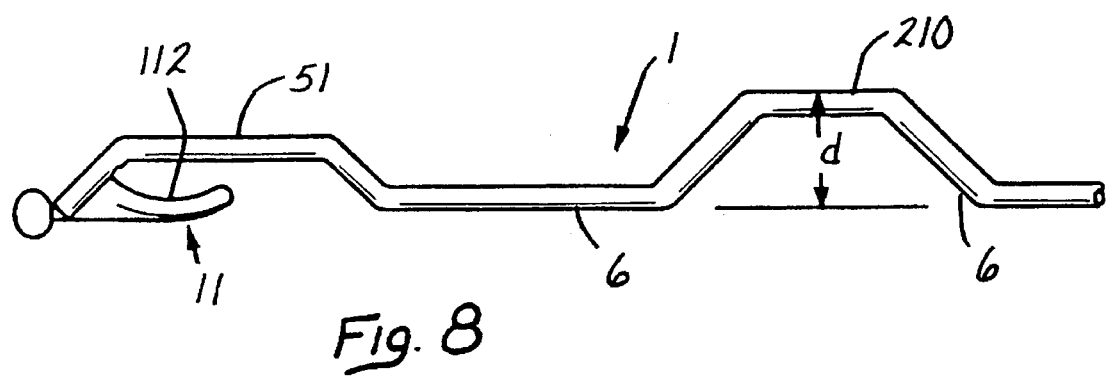
FIG. 8 is a side view of a valvulotome with a U-bend according to the invention to indicate the rotational orientation of the valvulotome.

FIGS. 6, 7, and 8 show some of the ways in which the valvulotome according to the invention can be adapted to enable its rotational orientation and position in the vein to be observed from outside the vein. FIGS. 6 and 7 show differential coloring, in which the extension 51 and the side of the tip 157 or 172 remote from the blade 11 are colored with a dark color. The dark color, which is shown by stippling 200 in FIGS. 6 and 7, contrasts with the shiny gold color of the blade 11. The contrast can be increased by coloring the tip 157 or 172 in a bright light color 205 on the side opposite to the dark-colored side. Preferred colors are black for the dark color and yellow for the light color. When the valvulotome is in the vein, the rotational orientation of the valvulotome can be determined by bringing the valvulotome into contact with the vein wall and observing the color through the vein wall. The difference between a yellow or gold part of the valvulotome and a black part of the valvulotome can be seen through the translucent wall of the vein.

FIG. 8 shows a variation on the valvulotome 1 for use in veins that are insufficiently translucent for the color orientation indicators just described to be observed. The shaft 6 is provided with a laterally-offset marker in the side of the shaft opposite to the blade 11. The laterally-offset marker is preferably provided by the U-bend 210 in the shaft 6. The U-bend 210 is made by making four bends in the shaft 6. The parts of the shaft 6 on opposite sides of the U-bend 210 should lie on the same longitudinal axis. The U-bend 210 is coplanar with the extension 51 and the blade 11, and lies on the same side of the shaft 6 as the extension 51. The depth d of the U-bend 210 is sightly larger than the diameter of the vein in which the valvulotome 1 is to be used. When the valvulotome 1 is inserted into the vein, the U-bend 210 causes the vein to flatten. The imprint of the U-bend 210 can be seen on the outside of the wall of the vein on one side of the vein and the imprint of the shaft 6 can be see on the outside of the wall of the vein on the opposite side of the vein. This unambiguously indicates the rotational orientation of the valvulotome: the cutting edge 112 of the blade faces the same side of the vein as the side on which the imprint of the U-bend 210 can be seen.

A further indication of the orientation of the valvulotome is provided by using an asymmetrical luer lock 21 (FIG. 1). The luer lock 21 can be provided with a flat 23. The luer lock is attached to the shaft 6 so that the flat 23 has a predetermined orientation relative to the blade 11. The preferred orientation of the flat 23 is perpendicular to the blade 11, and on the same side of the shaft 6 as the blade. The asymmetrical luer lock enables the surgeon to determine the orientation of the valvulotome in the vein by feeling the orientation of the flat 23 with his/her thumb or finger, or by observing the orientation of the flat 23.

FIG. 9 shows a variation on the valvulotome 301 that has a greater ability to self-locate in the vein. The valvulotome 301 is similar to the valvulotome 1 previously described except for the addition of two convex spring pieces. Components corresponding to those in the embodiment shown in FIG. 1 are indicated by the same reference numbers with 300 added. The first convex spring piece 303 is attached to the shaft 306. The second convex spring piece 308 is attached to the distal end of the third section 386 of the extension 351, extending out beyond the tip 357. The second convex spring piece 308 has a rounded nose 313 to prevent the spring piece from damaging the vein into which it is inserted. Both convex spring pieces are coplanar with the plane of the extension 351 and the blade 311 but are on the opposite side of the shaft 306 from the blade 311. The convex spring pieces 303 and 308 are preferably made from springy stainless steel and are spot welded to the shaft 306 and the third section 386. Alternatively springy plastic spring pieces 303 and 308 can be attached by means of a suitable adhesive.

The convex spring pieces 303 and 308 increase the overall width of the valvulotome 301 so that it is somewhat greater than the diameter of the vein into which the valvulotome 301 is to be inserted. The convex spring pieces 303 and 308 keep the tip 357, the shaft 306, and the back 302 of the blade in contact with the wall of the vein. This increases the possibility of the proximal end 327 of the blade entering a valve pocket when the valvulotome is withdrawn through the vein.

The convex spring pieces 303 and 308 can be attached to an operating lever (not shown) controlled from the proximal end of the valvulotome. The operating lever elongates the convex spring pieces, which lowers their profile. After the first leaflet of a valve is cut, the operating lever is operated to lower the profile of the convex spring pieces, which allows the valvulotome to be rotated more easily. After the valvulotome has been rotated, the operating lever is the operated once more to raise the convex spring pieces prior to cutting the second leaflet of the valve.

Preferred embodiments of the valvulotome according to the invention are shown in FIGS. 12A–12B and 13A–13B. In the preferred embodiment, the safety of the valvulotome is further increased by protecting the sharpened parts of the blade more intimately. Production is simplified by mounting the blade in a one-piece casting. The preferred embodiment also used a laterally-extending guide wire to move the cutter head laterally in the vein. This ensures engagement of the free end of the cutting blade with the valve leaflet prior to cutting the leaflet. The laterally extending guide wire is retractable and adjustable, so that the valvulotome can be used in veins of different diameters, and can also adapt to the change in diameter that occurs along the length of a single vein.

The valvulotome consists of three basic components: the cutting head 401, the operating handle 403, and the hollow shaft 405A or 405B. In the following description, a reference to the shaft 405 or the hollow shaft 405 will refer to the hollow shaft 405A or the hollow shaft 405B. The valvulotome 400A shown in FIGS. 12A–12B has a flexible shaft 405A and is for use in in-situ by-pass procedures; the valvulotome 400B shown in FIGS. 13A and 13B has the shorter, rigid shaft 405B, and is for disrupting the valves in vein segments to be used in CABG procedures. The operating handle 403 and the shaft 405A, 405B enable the surgeon to extend and retract the guide wire 407, as shown in FIG. 12B, when the cutting head 401 is in the vein and as will be described in more detail below.

Details of the cutting head 401 are shown in FIGS. 14A–14E. The vein cutter is mounted on the distal end of the shaft 405. The main components of the vein cutter are the haft 411 in which is mounted the cutting blade 413 The guide wire 407 extends from the shaft 405 into the slot 409 in the haft.

The haft 411 includes the substantially cylindrical central portion 415, on each end of which are the opposed frusto-conical portions 417 and 419. The haft is preferably a single casting of a suitable metal, preferably stainless steel. Aluminium is a suitable alternative. Alternatively, the haft may be a molding of a suitable plastic, such as fibre-reinforced polycarbonate, or may be machined from suitable metal or plastic stock.

The haft is preferably finished in a dark color, such as black. The orientation mark 455 is placed on the haft on the same side as the back of the blade. The orientation mark is of a contrasting color, for example, white, and enables the orientation of the cutting head to be seen through the translucent wall of the vein, or directly using angioscopy.

The distal frusto-conical portion 419 of the haft 411 terminates in the rounded nose 421. The relatively large, rounded nose 421 enables the cutting head 401 to be advanced up the vein without the risk of snagging side branches of the vein. The blind bore 423, which receives the distal end 425 of the guide wire 407, is formed inside the distal frusto-conical portion 419, as shown in FIG. 14F. The blade slot 427, in which the cutting blade 413 is mounted, is formed in the side of the distal frusto-conical portion. Finally, the distal part of the slot 409, which accommodates the guide wire 407, is formed in the side of the distal frusto-conical portion 419, opposite the blade slot 427.

The proximal frusto-conical portion 417 of the haft 411 is formed with the axial bore 429 which accommodates the shaft 405. Formed in the side of the distal portion of the proximal frusto-conical portion is the proximal part of the slot 409, which accommodates the guide wire 407 and communicates with the bore 429.

The central part of the slot 409, which accommodates the guide wire 407, is formed in the side of the central cylindrical portion 415 of the haft 411. The blade recess 431 is formed in the side of the haft 411, opposite the slot 409. As will be described in more detail below, the blade recess protects the vein wall from the sharpened edge 433 of the cutting blade. The blade recess also includes the shoulder 435 at its proximal end. As will be described in more detail below, the shoulder protects the vein wall from the proximal end 437 of the cutting blade.

The cutting blade 413 is flat and has a shape similar to that of the blade of a scythe, except that its free end 437 is rounded and is at least partially blunt. The cutting blade extends proximally from its fixed end 438 mounted in the blade slot 427 in the distal frusto-conical portion 419 of the haft, and terminates in the rounded free end 437. Most of the cutting blade lies within the blade recess 431. The cutting blade also includes the opposed flat sides 416 and 418, the sharpened edge 433 between the flat sides, and the dull back 439 between the flat sides, opposite the sharpened edge.

The sharpened edge 433 of the cutting blade faces into the blade recess 431, and is coplanar with the long axis of the haft 411. The sharpened edge 433 extends proximally from the deepest part of the blade recess, arcing outwards to a maximum spacing from the blade recess, and arcing back slightly into the blade recess at its proximal end, adjacent the free end 437. The proximal end of the sharpened edge 433 is spaced from the blade recess 431 by the spacing d, which is chosen to be wide enough to admit a vein leaflet, typically about 1 mm.

The back 439 of the cutting blade, remote from the sharpened edge 433, is blunt. The back of the cutting blade extends proximally from the junction 441 between the distal end of the blade recess 431 and the surface of the distal frusto-conical portion 419 of the haft 411, arcing slightly outwards to a maximum spacing from the blade recess, and arcing back into the blade recess towards its proximal end, adjacent the free end 437, such that the proximal end lies within the blade recess.

An end view of the free end 437 of the cutting blade 413 is shown in FIG. 14E. The free end 437 is approximately semi-circular, and includes an inwards-facing part 445, which faces the long axis of the haft 411, is sharp, and forms a continuation of the sharpened edge 433. The free end also includes a proximal-facing part 443, which faces proximally, is blunt, and forms a continuation of the blunt back 439. The proximal-facing part 443 of the free end is blunt to prevent it from accidentally cutting the vein wall if it comes into contact with the vein wall.

The shape of the cutting blade 413, and the mounting of the cutting blade in the blade recess 431 of the haft 411 are such that the cutting blade can be advanced or withdrawn in the vein with a negligible risk of the cutting blade accidentally cutting the vein, but can cut the vein leaflets completely when required to do so. When the cutting head 401 is advanced through the vein, the rounded nose 421 and gently curved sides of the haft 411 and the blunt back 439 of the cutting blade are presented to the vein wall. None of these parts is capable of cutting the vein wall. The haft 411 guards the vein wall from the sharpened edge 433 of the cutting blade 413. The back 439 of the cutting blade, which is blunt, bounds the vein cutter in the radial direction remote from the haft 411. Towards the free end 437, the cutting blade 413 curves inwards into the blade recess 431, where it is protected by the shoulder 435. The shoulder protects the vein wall from the free end 437 of the cutting blade 413, which is sharp over its inwards-facing part 445, when the cutting head 401 is withdrawn from the vein. Also, when the vein cutter is withdrawn, the shoulder 435 and the curve of the proximal portion of the cutting blade 413 into the blade recess 431 prevent the free end 437 of the cutting blade from accidentally entering side branches of the vein. This, in turn, prevents exposure of the vein wall to the sharpened edge 433 of the cutting blade. Finally, the spacing d between the proximal end of the sharpened edge 433 of the cutting blade and the blade recess 431 is chosen to be small enough to prevent parts of the vein other than the leaflet from entering the blade recess. This, in turn, prevents such parts of the vein from being exposed to the sharpened edge 433 of the cutting blade.

The sharpened edge 433 and the inwards-facing part 445 of the free end of the cutting blade are sharp, but the arrangement of the cutting blade 413 relative to the haft 411 ensures that the only portions of the vein that are exposed to these sharp edges are the vein leaflets that enter the blade recess 431. The way in which the valvulotome 400A or 400B cuts the vein leaflets will be described in detail below.

The cutting head 401 is mounted on the distal end of the hollow shaft 405, the proximal end of which is attached to the operating handle 403. In the embodiment shown in FIGS. 12A and 12B, the flexible hollow shaft 405A has a stainless-steel braid inner covered by a polyurethane sleeve. The braid inner improves the torque characteristics of the shaft 405A, but may be omitted if desired. The hollow shaft 405A is about 650 mm long with an outside diameter of about 1 mm and an internal diameter of about 0.6 mm. Distance marks 449 are provided at predetermined intervals of about 100 mm on the outer surface of the hollow shaft 405A to enable the surgeon the determine the location of the cutting head 401 relative to the insertion point of the shaft into the vein.

Figure 13A:
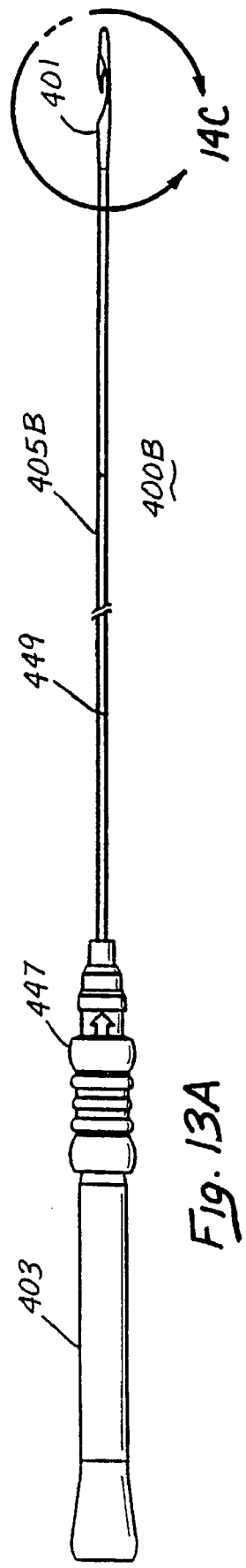
FIG. 13A is a view of a version of the preferred embodiment of the valvulotome according to the invention for use in distrupting the valves in vein segments to be used in CABG procedures.
Figure 13B:
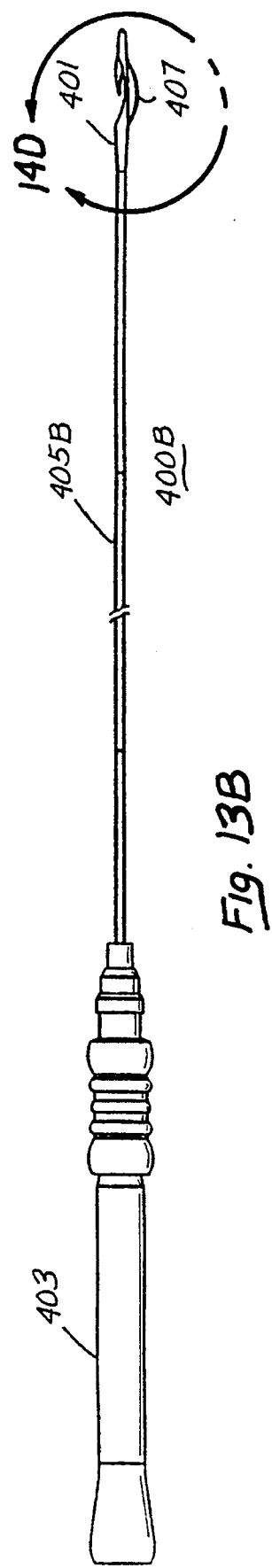
FIG. 13B is a view of the preferred embodiment of the valvulotome shown in FIG. 13A with its guide wire extended.

In the embodiment shown in FIGS. 13A and 13B, the hollow shaft 405B is a rigid stainless-steel tube about 30 cm long with an external diameter of about 1.0 mm and an internal diameter of about 0.6 mm. Distance marks 449 are provided at predetermined intervals on the outer surface of the hollow shaft 405B to enable the surgeon the determine the location of the cutting head 401 relative to the insertion point of the shaft into the vein.

The guide wire 407 runs from the operating handle 403 to the vein cutter 401 through the bore of the shaft 405. The guide wire is preferably a wire-wrapped single filament of stainless steel with an outside diameter of about 0.55 mm. The proximal end (not shown) of the guide wire is attached to the operating sleeve 447 of the operating handle 403. The surgeon slides the operating sleeve distally relative to the operating handle to extend the guide wire 407 radially from the vein cutter 401, and slides the operating sleeve proximally to retract the guide wire. Sliding the operating sleeve distally moves the guide wire distally relative to the shaft 405. The distal end 425 of the guide wire is fixed relative to distal end of the vein cutter 401, so the distal movement of the guide wire causes the guide wire to bow outwards from the slot 409 in the haft 411, as shown in FIGS. 14D and 14F. Indents (not shown) are provided between the operating sleeve 447 and the operating handle 403, so that the operating sleeve will stay in any one of the sliding positions that produces one of the intermediate extensions, such as the intermediate extension 451, or the full extension 453, of the guide wire shown in FIG. 14D. The selective adjustability of the guide wire extension enables the valvulotome according to the invention to be used in veins of differing diameters, and also enables the valvulotome to adapt to the change in diameter that occurs along the length of a single vein.

The cutting head 401 is advanced through the vein with the guide wire 407 retracted, as shown in FIGS. 12A and 13A. When the cutting head is withdrawn in the vein to cut the valve leaflet, the operating sleeve 447 on the operating handle 403 is operated to extend the guide wire 407 from the slot 409 in the back of the haft 411, as shown in FIGS. 12B and 13B. The guide wire contacts the vein wall, and forces the dull back 439 of the cutting blade 413 into contact with the opposite side of the vein wall. This ensures that, as the cutting head is further withdrawn, the valve leaflet to be cut will enter the blade recess 431, where it can be cut by the sharpened edge 433.

A method according to the invention of using the embodiment of the valvulotome 1 according to the invention shown in FIG. 1 to disrupt vein valves in the course of a coronary artery bypass procedure is illustrated in FIGS. 1 and 15A through 15H. The method can also be adapted for use in an in-situ bypass procedure.

A suitably-sized section of the saphenous vein V is removed from the leg and placed on a side table. The side branches, such as B1 and B2 are preferably tied off before the valvulotome 1 is used. This enables the vein to be inflated to determine the location of the valves. The syringe 26 is filled with physiologic solution 31, or some other suitable fluid, and the syringe 26 is screwed onto the luer hub 21. The resulting valvulotome assembly is shown in FIG. 1.

The surgeon places the vein V on the table, and holds it down with one hand. With the other hand, the surgeon carefully inserts the valvulotome 1 into the smaller-diameter end of the vein and advances the valvulotome 1 up the vein. Alternatively, the surgeon can hold the smaller-diameter end of the vein V with tweezers held in one hand.

By starting at the smaller-diameter end of the vein, the valvulotome is advanced in the normal direction indicated by the arrow 5. The valvulotome 1 therefore passes easily though the valves in the vein, such as the valve Va1 shown in FIG. 15A. The surgeon can monitor the progress of the valvulotome from outside the vein by observing the length of the shaft 6 projecting from the proximal end of the vein V. The position of the valvulotome can also be determined by observing the position of colored markings on the valvulotome 1 through the translucent wall of the vein or the imprint of the valvulotome on the vein wall if the vein wall is opaque.

Possible snagging of the valvulotome 1 on a flap on the intimal surface of the vein V as the valvulotome is advanced through the vein can be avoided by using an alternative method of advancing the valvulotome. The alternative method uses the version of the valvulotome 1 that includes the traction point 181 (FIG. 3A). According to the method, the surgeon holds the vein V using one hand, as described above, and threads a guide wire up the vein from the smaller-diameter end with the other hand. When the distal end of the guide wire reaches the larger-diameter end of the vein, the surgeon attaches one end of a piece of suture to the proximal end of the guide wire and, pulling on the distal end of the guide wire, pulls the suture through to the larger-diameter end of the vein V. The surgeon then attaches the other end of the suture to the traction point 181 of the valvulotome assembly. The surgeon then places the valvulotome assembly and the vein V in a linear arrangement on the table and introduces the distal end of the valvulotome 1 into the smaller-diameter end of the vein. The surgeon holds the smaller-diameter end of the vein V with tweezers held in one hand and gently pulls on the suture to advance the valvulotome assembly through the vein V towards its larger-diameter end.

With either method of advancing the valvulotome through the vein V, when the valvulotome reaches the larger-diameter end of the vein, the surgeon withdraws it slightly. The surgeon then grips the larger-diameter end of the vein V with forceps F held in the hand that formerly was holding the smaller-diameter end of the vein V, as shown in FIG. 1. The forceps F grip the vein so as to seal the larger-diameter end of the vein. The forceps F also can clamp the vein to a towel covering the table on which the vein is placed. This secures the larger-diameter end of the vein to the table and enables the surgeon to remove his/her hand from the forceps F when needed.

Figure 15A:
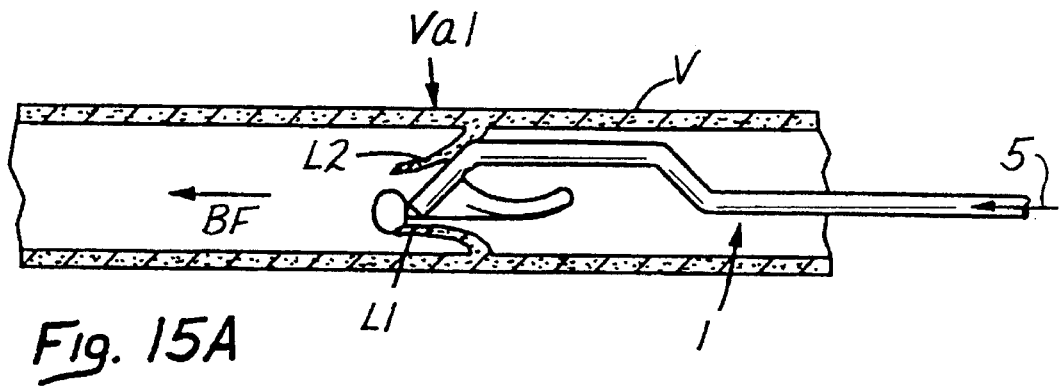
FIG. 15A shows part of a valvulotome according to the invention in a vein being advanced in the blood-flow direction through the vein.
Figure 15B:
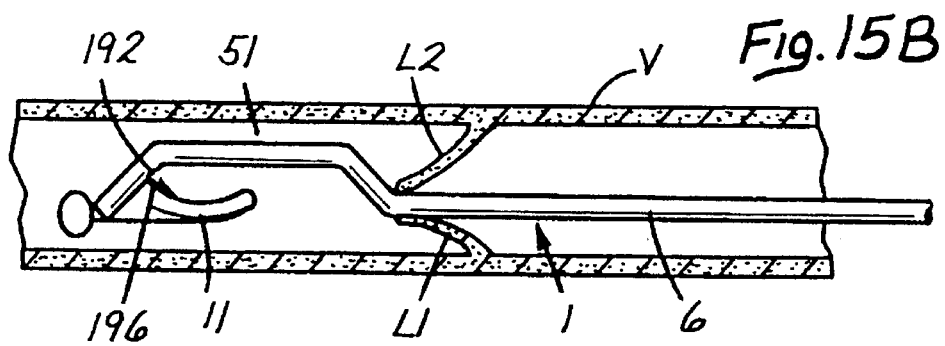
FIG. 15B shows part of a valvulotome according to the invention in a vein after it has been advanced past the most distal valve in the vein. Physiologic solution is emitted from the distal end of the valvulotome to inflate the vein.
Figure 15C:
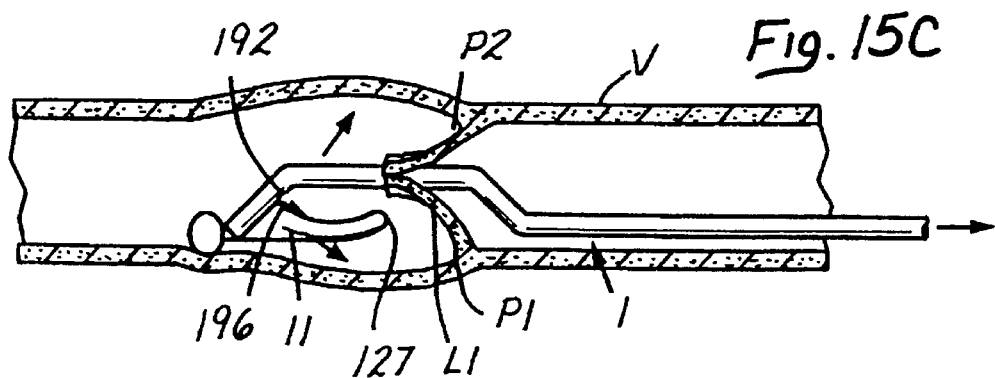
FIG. 15C shows part of a valvulotome according to the invention in a vein. Solution emitted from the valvulotome has inflated the vein to indicate the location of the most distal valve.

The surgeon then depresses the plunger 27 of the syringe 26. This forces physiologic solution out of the syringe 26, through the shaft 6, and out of the hole 192, to form the jet of solution indicated by the arrow 196, as shown in FIG. 15B. The solution entering the part of the vein between the forceps F and the most distal valve Va1 in the vein V creates a pressure differential across the valve Va1 and causes the valve Va1 to close around the shaft 6 of the valvulotome 1. Once the valve Va1 is closed, pressure builds up in the part of the vein between the forceps F and the valve Va1, causing the vein to inflate, as shown in FIG. 15C. The part of the vein below the valve Va1 is not pressurized, and therefore does not inflate. This enables the surgeon to determine the location of the valve Va1 along the length of the vein V. Providing irrigation through the valvulotome enables the valve cutting process to be carried out by a single surgeon without assistance. With conventional techniques, irrigation is introduced into the top of the vein which requires a third hand, i.e., that of an assistant.

Figure 15D:
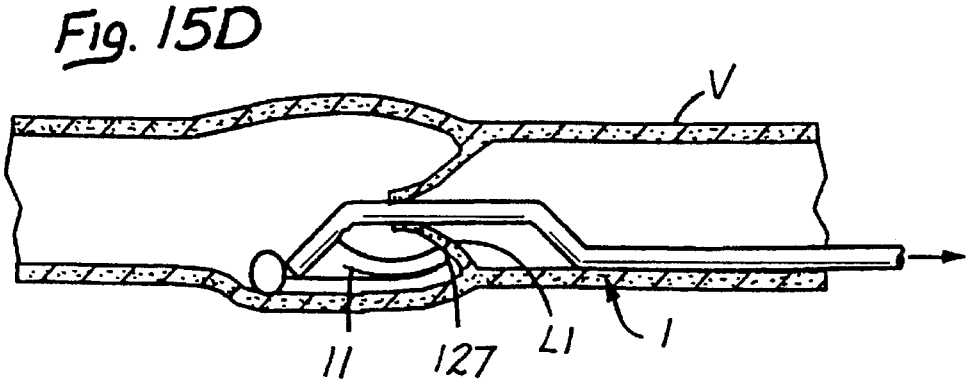
FIG. 15D shows part of a valvulotome according to the invention in a vein. The valvulotome has been withdrawn and the proximal end of its blade has engaged the first leaflet and is sliding up the first leaflet towards the apex of the first leaflet in the base of the valve pocket.

The surgeon observes the position of the extension 51 of the valvulotome 1 in the vein and withdraws the valvulotome 1 until the extension 51 is in the vicinity of the valve Va1. Holding the syringe 26 lightly, the surgeon carefully withdraws the valvulotome 1 until resistance is felt. This indicates that the proximal end 127 of the blade of the valvulotome has contacted one of the leaflets, say the leaflet L1, of the valve Va1. Further gentle withdrawing pressure brings the proximal end 127 of the blade into the valve pocket P1, as shown in FIG. 15D. The surgeon holds the valvulotome gently to allow the valvulotome assembly to rotate as the blade slides up the leaflet L1 to enable the proximal end 127 of the blade to enter into the valve pocket P1 as deeply as possible, and to be centered within the valve pocket.

Figure 15E:
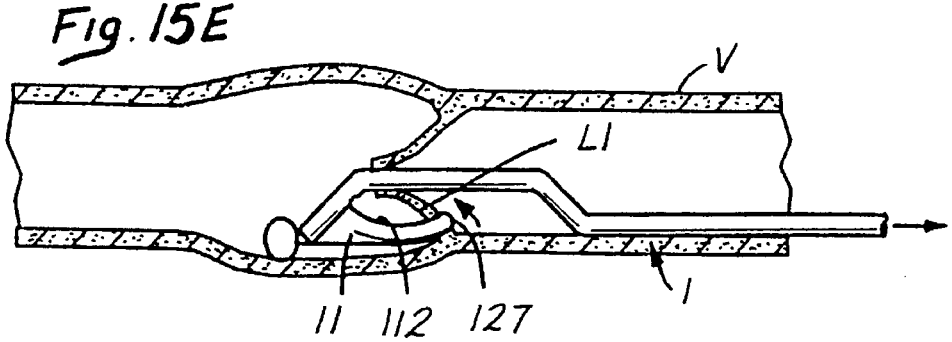
FIG. 15E shows part of a valvulotome according to the invention in a vein. The proximal end of the blade of the valvulotome has pierced the apex of the first leaflet. The curve of the blade fits snugly against the curve of the inflated vein. The arrow indicates the direction of propagation of the cut.
Figure 15F:
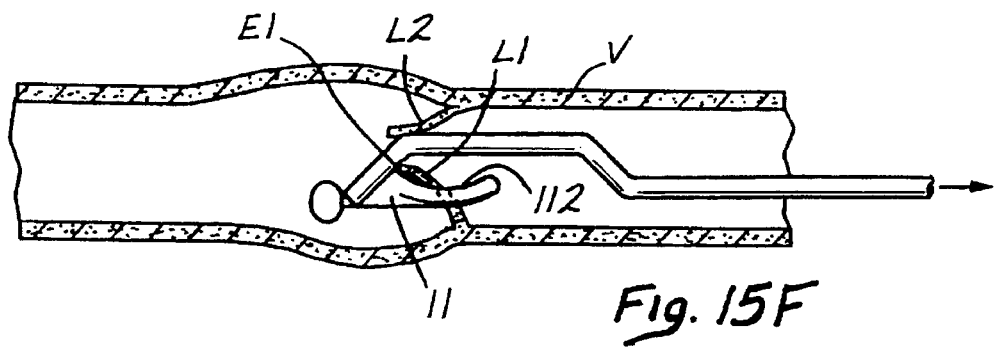
FIG. 15F shows part of a valvulotome according to the invention in a vein. The valvulotome has been further withdrawn and has cut through most of the first leaflet. In cutting the first leaflet, the valvulotome places the leaflet in tension enabling the leaflet easily to provide the resistance necessary for the blade to cut the leaflet cleanly.
Figure 15G:
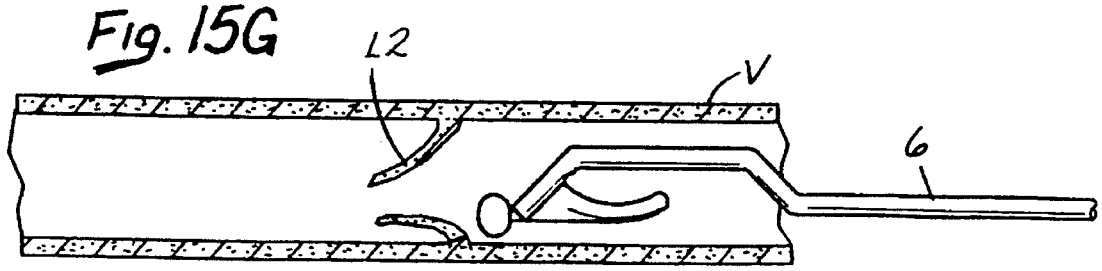
FIG. 15G shows part of a valvulotome according to the invention in a vein. The valvulotome has been further withdrawn and has cut through all of the first leaflet.

With the proximal end 127 of the blade located in the valve pocket, the surgeon applies greater withdrawing pressure to cause the proximal end of the blade to pierce the leaflet L1 at its apex, as shown in FIG. 15E. Once the proximal end of the blade has pierced through the leaflet, the leaflet is exposed to the sharp cutting edge 112 of the blade, which enables the withdrawing pressure to be reduced. The valvulotome assembly is then steadily withdrawn causing the cutting edge 112 of the blade to cut down the center of the leaflet towards the edge E, as shown in FIG. 15F. While cutting, the blade applies a tensile force in the direction away from the apex of the leaflet to the point being cut. The leaflet, being relatively strong in tension, provides the resistance necessary for cutting to take place. Finally, the blade 11 breaks through the edge E1 of the leaflet L1 substantially in the center of the leaflet, as shown in FIG. 15G, and the resistance to withdrawing the valvulotome assembly drops significantly.

The action of the valvulotome according to the invention is to be contrasted with the prior art Mills valvulotome shown in FIG. 11. The Mills valvulotome cuts the leaflet from the edge E towards the valve pocket P1, which places the leaflet in compression, in which direction the leaflet is weak. It is therefore much more difficult to obtain a clean cut up the center of the leaflet from edge of the leaflet to the valve pocket with the Mills valvulotome than to make a clean cut up the center of the leaflet from the valve pocket to the edge with the valvulotome according to the invention.

Figure 15H:
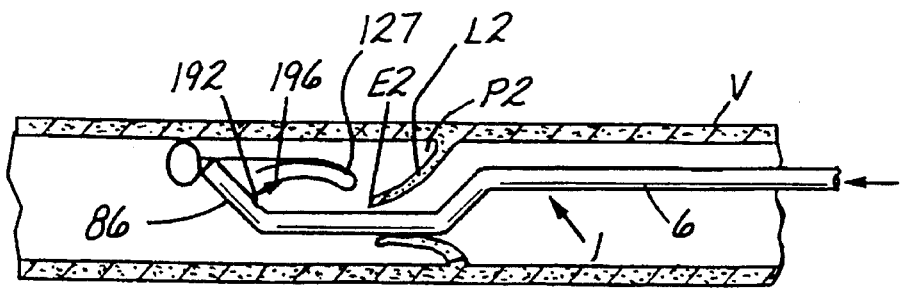
FIG. 15H shows part of a valvulotome according to the invention in a vein. The valvulotome has been axially rotated through 180 degrees and has been advanced back past the valve and is in position to cut the second leaflet of the valve. Solution is emitted from the valvulotome towards the second leaflet to separate the leaflet from the wall of the vein.

The surgeon then advances the valvulotome assembly 1 back up the vein V past the valve Va1. The surgeon can observe the position of the head of the valvulotome through the translucent wall of the vein. Once the blade of the valvulotome has passed the valve Va1, the surgeon rotates the syringe, and hence the valvulotome, through 180 degrees to align the blade with the second leaflet L2, as shown in FIG. 15H. If the cut first leaflet L1 has not allowed much of the solution to pass, and hence the vein above the valve Va1 is still pressurized, the surgeon can proceed with cutting the second leaflet L2 by withdrawing the valvulotome as described above.

In the more likely event that the cut first leaflet L1 has allowed substantially all the solution to pass and the vein above the valve Va1 is unpressurized, the surgeon once more depresses the plunger 27 of the syringe 26 (FIG. 1) to cause solution to be emitted from the hole 192 in the third section 86. A jet of solution indicated by the arrow 196 in FIG. 15H is emitted in the direction of the blade 11 which is aligned with the second leaflet L2. The force of the solution impinging on the leaflet L2 deflects the leaflet L2 away from the wall of the vein and bring it into contact with the shaft 6 of the valvulotome 1.

When the surgeon withdraws the valvulotome assembly, the edge E2 of the leaflet L2 enters the gap between the second portion 81 of the shaft and the proximal end 127 of the blade. Further withdrawal of the valvulotome assembly brings the proximal end 127 of the blade into the valve pocket P2, guided by the inner surface of the leaflet L2. Once the proximal end 127 of the blade has penetrated the valve pocket P2, the leaflet L2 is cut up its center as described above.

After both leaflets L1 and L2 of the valve Va1 have been cut, the surgeon depresses the plunger 27 of the syringe 26 once more to emit more solution into the vein. This pressurizes the part of the vein from the forceps F down to the next valve in the vein, Va2 (FIG. 1), and enables the surgeon to determine the position of the valve Va2. The surgeon cuts both leaflets of the valve Va2 using the procedure described above, and repeats the valve locating and cutting procedure described above until all the valves in the vein have been cut. The vein is then ready for use in a coronary artery bypass procedure.

The method according to the invention of using the preferred embodiment of the valvulotome according to the invention will be described next with reference to FIGS. 16A–16G. In the following description, use of the valvulotome 400A shown in FIG. 12A in the course of an in-situ procedure will be described. The method of using the valvulotome 400B to disrupt the valves in a vein segment to be used in a CABG procedure is similar, and will therefore not be described separately.

The cutting head 401 with the guide wire 407 in its retracted state is inserted into the smaller-diameter end of the vein V. The shaft 405 is manipulated to advance the vein cutter up the vein in the direction shown by the arrow 501, shown in FIG. 16A. The cutting head is advanced in the direction of normal blood flow, and the rounded nose 421 of the cutting head therefore passes easily though the valves in the vein, such as the valve Va1.

The position of the cutting head in the vein can be determined by observing the position of the distance marks 449 (FIG. 12A) on the shaft 405 relative to the point of insertion of the shaft into the vein. The position of the cutting head and its angular orientation in the vein can be determined by distally sliding the operating sleeve 447 in the operating handle 403 (FIG. 12A) to extend the guide wire 407. This presses the guide wire and the haft 411 against opposite portions of the vein wall, which can be seen from outside the vein. It can also be seen whether it is the guide wire or the haft that is in contact with the vein wall closest to the surgeon. This enables the angular orientation of the cutting head 401 to be determined and corrected, if necessary.

After the cutting head 401 has passed through the valve Va1, the operating sleeve 447 in the operating handle 403 (FIG. 12A) is slid distally to extend the guide wire 407, as indicated by the arrow 503. The guide wire contacts the vein wall and moves the cutting head 401 laterally, as indicated by the arrow 505. This brings the dull back 439 of the cutting blade 413 into contact with the vein wall, and brings the haft 411 into contact with the leaflet L1, as shown in FIG. 16B.

The shaft 405 is then manipulated to withdraw the cutting head 401 in the direction indicated by the arrow 507 in FIG. 16C. As the cutting head is withdrawn, the edge E of the leaflet L1 remains in contact with the proximal frusto-conical portion 417 of the haft 411. After the shoulder 435 of the blade recess 431 passes the edge E of the leaflet, the edge E slides into the blade recess. Further withdrawal of the shaft 405 brings the edge E of the leaflet into the gap between the haft 411 and the sharpened edge 433 of the cutting blade 413, as shown in FIG. 16D. This exposes part of the leaflet to the sharpened edge 433 of the cutting blade and to the sharp inwards-facing part 445 of the free end 437 of the cutting blade.

As the cutting head 401 is further withdrawn, the dull proximalfacing part 443 of the free end 437 of the cutting blade 413 slides up the back of the leaflet L1, and lodges in the valve pocket P1 between the leaflet L1 and the vein V, as shown in FIG. 16D. During this pan of the procedure, the surgeon holds the shaft 405 lightly to allow the cutting head to rotate as the free end of the cutting blade slides up the leaflet L1. This enables the free end 437 of the cutting blade to enter into the valve pocket P1 as deeply as possible, and centers the cutting blade on the leaflet.

Figure 16E:
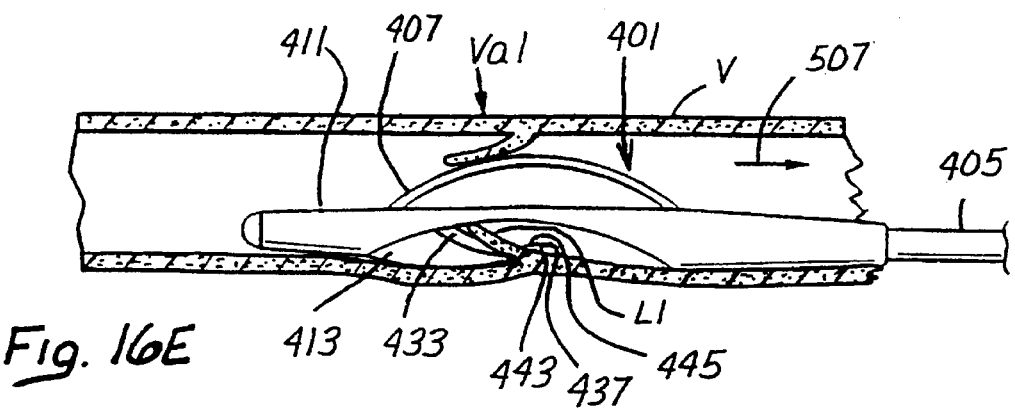
FIG. 16E shows part of the preferred embodiment of the valvulotome according to the invention in the vein being withdrawn through the valve after the free end of the cutting blade has penetrated the leaflet at the apex.
Figure 16F:
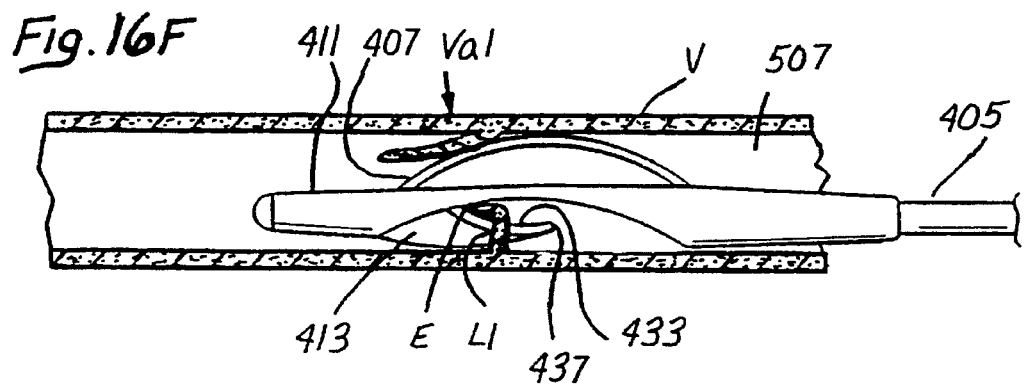
FIG. 16F shows pan of the preferred embodiment of the valvulotome according to the invention in the vein being withdrawn through the valve with the sharpened edge of the cutting blade slicing through the leaflet from apex to edge.

With the dull proximal-facing part 443 of the free end 437 of the cutting blade 413 located deep in the valve pocket, the shaft 405 is further manipulated to withdraw the cutting head 401 further. This causes the dull proximal-facing pan 443 of the free end 437 of the cutting blade 413 to pierce the leaflet L1 at its apex in the valve pocket P1, as shown in FIG. 16E. Once the dull proximal-facing part of the free end of the cutting blade has pierced through the leaflet, the leaflet is exposed to the sharpened edge 433 of the cutting blade. The cutting head is then further withdrawn, causing the sharpened edge 433 of the cutting blade to cut down the center of the leaflet from the apex towards the edge E, as shown in FIG. 16F.

While cutting, the cutting blade 413 applies a tensile force to the leaflet L1 in the direction away from the apex of the leaflet towards the point of contact between the cutting blade and the leaflet. The leaflet is relatively strong in tension, and so can provide the resistance necessary for cutting to take place. Finally, the cutting blade 433 breaks through the edge E of the leaflet L1, substantially in the center of the leaflet.

Figure 16G:
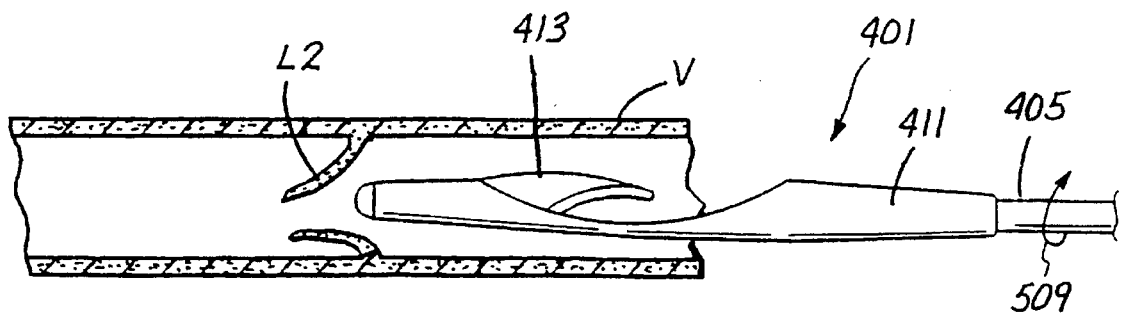
FIG. 16G shows part of the preferred embodiment of the valvulotome according to the invention after it has cut the first leaflet of the valve, and prior being rotated through 180 degrees to cut the second leaflet of the valve.

After the first leaflet is cut, the operating sleeve 447 on the operating handle 403 (FIG. 12A) is slid proximally to retract the guide wire 407, the shaft 405 is manipulated to rotate the cutting head 401 through 180 degrees about its long axis, as shown by the arrow 509 in FIG. 16G. The shaft 5 is then manipulated to advance the cutting head up the vein V past the valve Va1 a second time to cut the leaflet L2 by means of the steps illustrated in FIGS. 16B–16G.

Although illustrative embodiments of the invention have been described herein in detail, it is to be understood that the invention is not limited to the precise embodiments described, and that various modifications may be practiced within the scope of the invention defined by the appended claims.

We claim:

1. A valvulotome for disrupting the valves of a vein, the valvulotome comprising:

an elongate blade mounting member defining an axis, the blade mounting member including a distal portion;

a thin, scythe-shaped cutting blade defining a plane, the cutting blade being mounted relative to the blade mounting member with the plane on the axis, the cutting blade including:

a fixed end fixedly attached to the distal portion of the blade mounting member, a sharpened edge facing towards the blade mounting member, arcing outwards and proximally from the distal portion of the blade mounting member, and terminating in a proximal portion spaced from the blade mounting member, a blunt back edge opposite the sharpened edge, and a free end opposite the fixed end, the free end connecting the blunt back edge to the proximal portion of the sharpened edge and including a blunt proximal-facing portion forming a continuation of the blunt back edge; and wherein a portion of the blade mounting member proximal of the distal portion is shaped to provide a blade recess accommodating the sharpened edge and the free end of the cutting blade.

2. The valvulotome of claim 1, wherein the blade recess includes a proximal portion shaped to provide a shoulder adjacent, and spaced from, the free end of the cutting blade.

3. A valvulotome for disrupting the valves of a vein, the valvulotome comprising:

an elongate blade mounting member defining an axis, the blade mounting member including a distal portion;

a thin, scythe-shaped cutting blade defining a plane, the cutting blade being mounted relative to the blade mounting member with the plane on the axis, the cutting blade including:

a fixed end fixedly attached to the distal portion of the blade mounting member, a sharpened edge facing towards the blade mounting member, arcing outwards and proximally from the distal portion of the blade mounting member, and terminating in a proximal portion spaced from the blade mounting member, a blunt back edge opposite the sharpened edge, and a free end opposite the fixed end, the free end connecting the blunt back edge to the proximal portion of the sharpened edge and including a blunt proximal-facing portion forming a continuation of the blunt back edge; and extendable means for selectively moving the cutting blade laterally in the vein.

4. The valvulotome of claim 3, wherein:

the blade mounting member includes a surface opposite the cutting blade and a bore communicating with a slot formed in the surface; and the extendable means comprises:

a guide wire slidably mounted in the bore and including an extending portion adjacent the slot, and means for selectively sliding a proximal portion of the guide wire relative to the bore, the selective sliding selectively extending the extending portion of the guide wire from the slot.

5. A valvulotome for disrupting the valves of a vein, the valvulotome comprising:

an elongate blade mounting member defining an axis, the blade mounting member including a distal portion;

a thin, scythe-shaped cutting blade defining a plan, the cutting blade being mounted relative to the blade mounting member with the plane on the axis, the cutting blade including:

a fixed end fixedly attached to the distal portion of the blade mounting member, a sharpened edge facing towards the blade mounting member, arcing outwards and proximally from the distal portion of the blade mounting member, and terminating in a proximal portion spaced from the blade mounting member, a blunt back edge opposite the sharpened edge, and a free end opposite the fixed end, the free end connecting the blunt back edge to the proximal portion of the sharpened edge and including a blunt proximal-facing portion forming a continuation of the blunt back edge;

wherein the blade mounting member further comprises:

an elongate shaft, defining the axis and having a distal portion; and an extension extending distally from the distal portion of the shaft in a laterally offset relation thereto, the extension including a distal portion whereto the fixed end of the cutting blade is fixedly attached; and wherein the extension is shaped to provide a blade recess accomodating the sharpened edge and the free end of the cutting blade.

6. The valvulotome of claim 5, wherein the extension is further shaped to provide a shoulder adjacent, and spaced from, the free end of the cutting blade.

7. A valvulotome for disrupting the valves of a vein, the valvulotome comprising:

an elongate blade mounting member defining an axis, the blade mounting member including a distal portion;

a thin, scythe-shaped cutting blade defining a plane, the cutting blade being mounted relative to the blade mounting member with the plane on the axis, the cutting blade including:
   a fixed end fixedly attached to the distal portion of the blade mounting member,
   a sharpened edge facing towards the blade mounting member, arcing outwards and proximally from the distal portion of the blade mounting member, and terminating in a proximal portion spaced from the blade mounting member,
   a blunt back edge opposite the sharpened edge, and
   a free end opposite the fixed end, the free end connecting the blunt back edge to the proximal portion of the sharpened edge and including a blunt proximal-facing portion forming a continuation of the blunt back edge;
wherein the blade mounting member further comprises:
   an elongate shaft, defining the axis and having a distal portion; and
   an extension extending distally from the distal portion of the shaft in a laterally offset relation thereto, the extension including a distal portion whereto the fixed end of the cutting blade is fixedly attached; and
extendable means for selectively moving the cutting blade laterally in the vein.

8. A valvulotome for disrupting the valves of a vein, the valvulotome comprising:
an elongate blade mounting member defining an axis, the blade mounting member including a distal portion;
a thin, scythe-shaped cutting blade defining a plane, the cutting blade being mounted relative to the blade mounting member with the plane on the axis, the cutting blade including:
   a fixed end fixedly attached to the distal portion of the blade mounting member,
   a sharpened edge facing towards the blade mounting member, arcing outwards and proximally from the distal portion of the blade mounting member, and terminating in a proximal portion spaced from the blade mounting member,
   a blunt back edge opposite the sharpened edge, and
   a free end opposite the fixed end, the free end connecting the blunt back edge to the proximal portion of the sharpened edge and including a blunt proximal-facing portion forming a continuation of the blunt back edge; and
wherein the blade mounting member further comprises:
   an elongate shaft, defining the axis and having a distal portion; and
   a substantially cylindrical haft extending distally from the distal portion of the shaft, the haft including:
      a blunt nose remote from the elongate shaft,
      a curved surface,
      a blade recess formed in the curved surface, and
      a distal portion whereto the fixed end of the sharpened blade is fixedly attached with the cutting edge and the free end in the blade recess.

9. The valvulotome of claim 8, wherein the blade recess includes a proximal portion shaped to provide a shoulder adjacent, and spaced from, the free end of the cutting blade.

10. The valvulotome of claim 8, additionally comprising means for moving the cutting blade laterally in the vein.

11. The valvulotome of claim 10, wherein:
the curved surface includes a portion opposite the cutting blade;

the haft includes a bore communicating with a slot formed in the curved surface; and
the extendable means comprises:
   a guide wire slidably mounted in the bore and including an extending portion adjacent the slot, and
   means for selectively sliding a proximal portion of the guide wire relative to the bore, the selective sliding selectively extending the extending portion of the guide wire from the slot.

12. A valvulotome for disrupting the valves of a vein, the valvulotome comprising:
an elongate blade mounting member defining an axis, the blade mounting member including a distal portion;
a thin, scythe-shaped cutting blade defining a plane, the cutting blade being mounted relative to the blade mounting member with the plane on the axis, the cutting blade including:
   a fixed end fixedly attached to the distal portion of the blade mounting member,
   a sharpened edge facing towards the blade mounting member, arcing outwards and proximally from the distal portion of the blade mounting member, and terminating in a proximal portion spaced from the blade mounting member,
   a blunt back edge opposite the sharpened edge, and
   a free end opposite the fixed end, the free end connecting the blunt back edge to the proximal portion of the sharpened edge and including a blunt proximal-facing portion forming a continuation of the blunt back edge; and
wherein the cutting blade includes opposed sides perpendicular to the blunt back edge, the sides being wider at the fixed end of the cutting blade than at the free end of the cutting blade.

13. A valvulotome for disrupting the valves of a vein, the valvulotome comprising:
an elongate shaft defining an axis, the shaft including a distal end;
a substantially cylindrical haft extending distally from the distal end of the shaft and terminating in a blunt nose, the haft including:
   a distal portion,
   a curved surface,
   a blade recess formed in the curved surface, and
   a bore communicating with a slot formed in a portion of
the curved surface opposite the blade recess;
a thin, scythe-shaped cutting blade defining a plane, the cutting blade being mounted relative to the haft with the plane on the axis, the cutting blade including:
   a fixed end fixedly attached to the distal portion of the haft,
   a sharpened edge facing into the blade recess, arcing outwards and proximally from the distal portion of the haft, and terminating in a proximal portion in the blade recess and accommodated thereby,
   a blunt back edge opposite the sharpened edge, and
   a free end opposite the fixed end, the free end connecting the blunt back edge to the proximal portion of the sharpened edge and including a blunt proximal-facing portion forming a continuation of the blunt back edge;
a guide wire slidably mounted in the bore and including an extending portion adjacent the slot; and
means for selectively sliding a proximal portion of the guide wire relative to the bore, the selective sliding selectively extending the extending portion of the guide wire from the slot.

14. The valvulotome of claim 13, wherein the blade recess includes a proximal portion shaped to provide a shoulder adjacent, and spaced from, the free end of the cutting blade.

15. The valvulotome of claim 13, wherein the cutting blade includes opposed sides perpendicular to the blunt back edge, the sides being wider at the fixed end of the cutting blade than at the free end of the cutting blade.

16. A method of performing a valvotomy in a vein having a valve comprising a leaflet joined to the vein, the leaflet and the vein forming a valve pocket having an apex, the leaflet including an edge remote from the apex, the method comprising the steps of:

provided a valvulotome including:
an elongate blade mounting member defining an axis and including a distal portion, and
a thin, scythe-shaped cutting blade defining a plane and being mounted relative to the blade mounting member with the plane on the axis, the cutting blade including:
a fixed end fixedly attached to the distal portion of the blade mounting member;
a sharpened edge facing towards the blade mounting member, arcing outwards and proximally from the distal portion of the blade mounting member, and terminating in a proximal portion spaced from the blade mounting member;
a blunt back edge opposite the sharpened edge; and
a free end opposite the fixed end, the free end connecting the blunt back edge to the proximal portion of the sharpened edge and including a blunt proximal-facing portion forming a continuation of the blunt back edge;

moving the cutting blade towards the valve to locate the free end of the cutting blade at the apex;

piercing the leaflet at the apex using a sharpened portion of the free end of the cutting blade; and applying a tensile force between the cutting blade and the leaflet to cut the leaflet from the apex to the edge.

17. The method of claim 16, wherein, in the step of providing a valvulotome, a valvulotome is provided wherein a portion of the blade mounting member proximal of the distal portion is shaped to provide a blade recess accommodating the sharpened edge and the free end of the cutting blade.

18. The method of claim 17, wherein, in the step of providing a valvulotome, a valvulotome is provided wherein the blade recess includes a proximal portion shaped to provide a shoulder adjacent, and spaced from, the free end of the cutting blade.

19. The method of claim 16, wherein:

in the step of providing a valvulotome, a valvulotome is provided additionally including an extendable guide wire mounted on a side of the blade mounting member remote from the cutting blade, the extendable guide wire being in a retracted state; and the step of moving the cutting blade towards the valve to locate the free end of the cutting blade at the apex includes the step of selectively extending the extendable guide wire to an extended state to move the cutting blade laterally in the vein.

20. The method of claim 19, wherein, in the step of selectively extending the extendable guide wire to an extended state, the extendable guide wire is selectively extended to the extended state wherein the back edge of the cutting blade contacts the vein wall.

21. The method of claim 16, wherein, in the step of providing a valvulotome, a valvulotome is provided wherein the blade mounting member comprises:

an elongate shaft, defining the axis and having a distal portion; and an extension extending distally from the distal portion of the shaft in a laterally offset relation thereto, the extension including a distal portion whereto the fixed end of the cutting blade is fixedly attached.

22. The method of claim 16, wherein, in the step of providing a valvulotome, a valvulotome is provided wherein the blade mounting member comprises:

an elongate shaft, defining the axis and having a distal portion; and a substantially cylindrical haft extending distally from the distal portion of the shaft, the haft including:
a blunt nose remote from the elongate shaft,
a curved surface,
a blade recess formed in the curved surface, and
a distal portion whereto the fixed end of the cutting blade is fixedly attached with the cutting edge and the free end in the blade recess.

23. The method of claim 16 wherein:

in the step of moving the cutting blade towards the valve, the blade mounting member is moved until the free end of the cutting blade contacts the leaflet, and advances along the leaflet to the apex;

in the step of piercing the leaflet, the blade mounting member is further moved until the free end pierces the leaflet at a point; and in the step of applying a tensile force between the cutting blade and the leaflet to cut the leaflet, the blade mounting member is withdrawn yet further to pull the cutting edge of the cutting blade through the leaflet from the point where the leaflet was pierced to the edge of the leaflet.

24. The method of claim 16, wherein:

the method is for cutting the leaflet substantially along the center of the leaflet;

the apex of the valve pocket corresponds to the center of the leaflet and is most proximal; and wherein:
the step of moving the cutting blade towards the valve includes the step of allowing the valvulotome to rotate axially to locate the free end of the cutting blade in the apex of the valve pocket.

25. The method of claim 16, wherein:

in the step of providing a valvulotome, a valvulotome additionally including a traction point is provided; and the step of moving the cutting blade towards the valve includes the steps of:
providing a suture,
advancing the suture through the vein,
attaching the suture to the traction point,
drawing on the suture to pull the valvulotome through the vein until the cutting blade has passed through the valve, and
withdrawing the blade mounting member to move the cutting blade towards the valve.

26. The method of claim 25, wherein the step of advancing the suture through the vein includes the steps of:

providing a catheter;

advancing the catheter through the vein;

attaching the suture to the catheter; and withdrawing the catheter from the vein to advance the suture through the vein.

27. The method of claim 25, wherein the step of inserting the suture into the vein includes the steps of:

providing a viewing scope having a field of view and a focal plane;

advancing the viewing scope through the vein;

attaching the suture to the viewing scope; and withdrawing the viewing scope from the vein to advance the suture and the valvulotome through the vein, the suture maintaining the cutting blade in the field of view and the focal plane of the viewing scope.

28. The method of claim 16, wherein:

the vein has a distal end;

the method additionally includes the step of providing fluid; and the step of moving the cutting blade towards the valve includes the steps of:

gripping the vein adjacent the distal end to seal the vein, advancing the valvulotome through the vein to a point adjacent the distal end, emitting the fluid from the valvulotome to inflate part of the vein between the distal end and the valve, and determining the position of the valve in the vein by observing the inflated part of the vein.

29. The method of claim 16, wherein:

the method additionally includes the step of providing fluid; and prior to the step of moving the cutting blade towards the valve, the method additionally comprises the step of emitting the fluid from the valvulotome to impinge on the leaflet adjacent to the cutting blade to displace the leaflet away from the vein.

30. The method of claim 16, wherein the vein includes a proximal end and a distal end, and the method is performed by a surgeon having a first hand and a second hand, and wherein:

the method additionally includes the step of providing fluid;

prior to the step of moving the cutting blade towards the valve, the method additionally comprises the steps of:

holding the proximal end of the vein in the first hand, holding the blade mounting member in the second hand, inserting the cutting blade into the proximal end of the vein, and advancing the cutting blade through the valve, moving the first hand to grip and seal the distal end of the vein, and with the second hand, causing the valvulotome to emit the fluid, the fluid inflating the vein; and in the step of moving the cutting blade towards the valve, the blade mounting member is withdrawn using the second hand to cut the valve.

31. The method of claim 30, wherein:

the method additionally comprises the step of providing a table having a cloth cover;

the step of holding the proximal end of the vein in the first hand additionally includes the step of placing the vein on the cloth cover on the table; and the step of moving the first hand to grip and seal the distal end of the vein additionally includes the step of clamping the distal end of the vein to the cloth cover.

* * * * *